US010729632B2

(12) United States Patent
Fletcher et al.

(10) Patent No.: US 10,729,632 B2
(45) Date of Patent: Aug. 4, 2020

(54) SWEETNER COMPOSITIONS

(71) Applicant: Tate & Lyle Ingredients Americas LLC, Hoffman Estates, IL (US)

(72) Inventors: Joshua Nehemiah Fletcher, Hoffman Estates, IL (US); Jason C. Cohen, Hoffman Estates, IL (US); Adrienne Stucky Pohrte, Hoffman Estates, IL (US)

(73) Assignee: Tate & Lyle Ingredients Americas LLC, Hoffman Estates, IL (US)

( * ) Notice: Subject to any disclaimer, the term of this patent is extended or adjusted under 35 U.S.C. 154(b) by 0 days.

(21) Appl. No.: 14/909,342

(22) PCT Filed: Jul. 31, 2014

(86) PCT No.: PCT/GB2014/052344
§ 371 (c)(1),
(2) Date: Feb. 1, 2016

(87) PCT Pub. No.: WO2015/015209
PCT Pub. Date: Feb. 5, 2015

(65) Prior Publication Data
US 2016/0198751 A1 Jul. 14, 2016

Related U.S. Application Data

(60) Provisional application No. 61/861,726, filed on Aug. 2, 2013.

(51) Int. Cl.
| A23L 27/30 | (2016.01) |
| A61K 8/60 | (2006.01) |
| A23L 2/60 | (2006.01) |
| A61Q 11/00 | (2006.01) |
| A23L 27/00 | (2016.01) |

(52) U.S. Cl.
CPC ............... *A61K 8/602* (2013.01); *A23L 2/60* (2013.01); *A23L 27/30* (2016.08); *A23L 27/32* (2016.08); *A23L 27/36* (2016.08); *A23L 27/37* (2016.08); *A23L 27/86* (2016.08); *A23L 27/88* (2016.08); *A61K 8/60* (2013.01); *A61Q 11/00* (2013.01); *A23V 2002/00* (2013.01)

(58) Field of Classification Search
CPC .... A23L 27/30; A23L 27/88; A23V 2200/204
See application file for complete search history.

(56) References Cited

U.S. PATENT DOCUMENTS

| 5,126,151 | A | 6/1992 | Bodor et al. |
| 5,411,756 | A | 5/1995 | Downton |
| 7,851,000 | B2 | 12/2010 | Boghani et al. |
| 8,287,897 | B2 | 10/2012 | Fukui |
| 8,679,461 | B2 | 3/2014 | Ley et al. |
| 8,993,027 | B2 | 3/2015 | Prakash et al. |
| 9,011,956 | B2 | 4/2015 | Prakash et al. |
| 2004/0086605 | A1 | 5/2004 | Sox |
| 2006/0003053 | A1 | 1/2006 | Ekanayake |
| 2007/0116819 | A1 | 5/2007 | Prakash |
| 2007/0116822 | A1 | 5/2007 | Prakash et al. |
| 2007/0116825 | A1 | 5/2007 | Prakash |
| 2007/0116828 | A1 | 5/2007 | Prakash |
| 2007/0116834 | A1 | 5/2007 | Prakash |
| 2008/0260925 | A1 | 10/2008 | Zink |
| 2009/0304891 | A1 | 12/2009 | Fujihara |
| 2010/0233102 | A1 | 9/2010 | Krammer |
| 2010/0278993 | A1 | 11/2010 | Prakash et al. |
| 2011/0160311 | A1 | 6/2011 | Prakash |
| 2012/0156351 | A1 | 6/2012 | Miyazawa et al. |
| 2012/0189739 | A1 | 7/2012 | Rathke et al. |
| 2012/0264831 | A1 | 10/2012 | Bridges |
| 2013/0052278 | A1 | 2/2013 | Rich et al. |
| 2015/0189904 | A1 | 7/2015 | Prakash et al. |
| 2016/0198749 | A1 | 7/2016 | Fletcher et al. |
| 2016/0198751 | A1 | 7/2016 | Fletcher et al. |

FOREIGN PATENT DOCUMENTS

| CN | 1207898 A | 2/1999 |
| CN | 1230099 A | 9/1999 |
| CN | 1780563 A | 5/2006 |
| CN | 101179955 A | 5/2008 |
| CN | 101309599 A | 11/2008 |
| CN | 102481004 A | 5/2012 |
| EP | 0891776 A1 | 1/1999 |
| EP | 1669090 | 6/2006 |
| EP | 2471383 | 7/2012 |
| GB | 2185674 | 7/1987 |
| JP | 01168248 A | 7/1989 |
| JP | H0710570 A | 1/1995 |
| JP | 2000197462 A | 7/2000 |
| JP | 2002514393 A | 5/2002 |
| JP | 2006223104 A | 8/2006 |
| JP | 2009502153 A | 1/2009 |
| JP | 2009505635 A | 2/2009 |
| JP | 2009517021 A | 4/2009 |
| JP | 2009517022 A | 4/2009 |
| JP | 2009517027 A | 4/2009 |
| JP | 2009517037 A | 4/2009 |
| JP | 2010527611 A | 8/2010 |
| JP | 2011024428 A | 2/2011 |
| JP | 2011045305 A | 3/2011 |
| JP | 2012110351 A | 6/2012 |
| JP | 2012130336 A | 7/2012 |
| JP | 2012235790 | 12/2012 |
| JP | 2013515492 A | 5/2013 |
| JP | 2013243970 | 12/2013 |
| JP | 2016529893 A | 9/2016 |

(Continued)

OTHER PUBLICATIONS

"Position of the American Dietetic Association: Use of nutritive and non nutritive sweeteners" Journal of the American Diet Association; 2004; 104 (2) pp. 255-275.

(Continued)

*Primary Examiner* — Theodore R. West
(74) *Attorney, Agent, or Firm* — RatnerPrestia

(57) ABSTRACT

A sweetener composition comprising: at least one sweetener; at least one anti-foaming agent; and at least one flavour enhancer, wherein the flavour enhancer is: at least one high potency sweetener that contains hydrophilic and hydrophobic structural moieties; and used in an amount below its sweetness threshold.

44 Claims, 6 Drawing Sheets

(56) References Cited

FOREIGN PATENT DOCUMENTS

| WO | 9802049 A1 | 1/1998 |
|---|---|---|
| WO | 9930577 | 6/1999 |
| WO | 9957990 A1 | 11/1999 |
| WO | 0057726 A1 | 10/2000 |
| WO | 2004095952 A1 | 11/2004 |
| WO | 2005025622 A1 | 3/2005 |
| WO | 2006072921 | 7/2006 |
| WO | 2006127934 | 7/2006 |
| WO | 2006127935 A1 | 11/2006 |
| WO | 2007061753 A2 | 5/2007 |
| WO | 2007061795 A1 | 5/2007 |
| WO | 2007081442 A2 | 7/2007 |
| WO | 2007107596 A1 | 9/2007 |
| WO | 2008049256 | 5/2008 |
| WO | 2008147727 A1 | 12/2008 |
| WO | 2008148239 | 12/2008 |
| WO | 2011009081 | 1/2011 |
| WO | 2011090709 A1 | 7/2011 |
| WO | 2011110930 | 9/2011 |
| WO | 2011127771 A1 | 9/2011 |
| WO | 2012088169 | 6/2012 |
| WO | 2012102769 | 8/2012 |
| WO | 2012128775 | 9/2012 |
| WO | 2012171086 | 12/2012 |
| WO | 2012171087 | 12/2012 |
| WO | 2012171087 A1 | 12/2012 |
| WO | 2015015210 A1 | 2/2015 |

OTHER PUBLICATIONS

Anonymous: "Neonesperidin dihydrochalcone", internet archive waybackmachine, Apr. 26, 2013 (Apr. 26, 2013), XP002731335, Retrieved from the Internet: URL:https://web.archive.org/web/2013042613 1353/http://en.wikipedia.org/wiki/Neohespe ridin_dihydrochalcone [retrieved on Oct. 16, 2014].
Great Britain Search Report for Great Britain Application No. GB1315558.5 dated Feb. 21, 2014.
Griffin, W.C. "Calculation of HLB Values of Non-Ionic Surfactants", Atlas Powder Company, Wilmington, Delaware, Journal of the Society of Cosmetic Chemists, vol. 5, No. 4, 1954, pp. 249-256.
Griffin, W.C. "Classification of Surface-Active Agents by "HLB"", Atlas Powder Company, Wilmington, Delaware, Journal of the Society of Cosmetic Chemists, vol. 1, No. 5, 1949, pp. 311-226.
International Preliminary Report on Patentability for International Application No. PCT/GB2014/052344 dated Feb. 2, 2016.
International Search Report for International Application No. PCT/GB2014/052344 dated Nov. 7, 2014.
Written Opinion of the International Searching Authority for International Application No. PCT/GB2014/052344 dated Nov. 7, 2011.
Chinese Office Action for Chinese Application No. 201480043810.3, dated Jul. 21, 2017 with translation, 46 pages.
Low et al., "Psychophysical Evaluation of Sweetness Functions Across Multiple Sweeteners", Chemical Senses, 2017, vol. 42, pp. 111-120.
European Communication Pursuant to Article 94(3) for European Application No. 14750251.2, dated Apr. 11, 2018, 10 pages.
Chinese Office Action for Chinese Application No. 201480043812.2, dated Oct. 31, 2018 with partial translation, 17 pages.
Third Party Observations for Application No. 2016-530611, dated Nov. 11, 2017, including English language translation, 19 pages.
Presentation of Information to JPO for Japanese Application No. 2016-530611, dated Nov. 24, 2016 with translation, 4 pages.
Chinese Office Action for Chinese Application No. 201480043812.2, dated Jul. 13, 2017, including English translation, 30 pages.
GB SSearch Report and Examination Report issued in related GB Application No. 1315559.3, dated Feb. 19, 2014, 4 pages.
International Preliminary Report on Patentability issued in related International Application No. PCT/GB2014/052345, dated Feb. 2, 2016, 10 pages.
International Search Report and Written Opinion issued in related International Application No. PCT/GB2014/042345, dated Nov. 7, 2014, 17 pages.
Final Office Action for U.S. Appl. No. 14/909,351, dated Mar. 8, 2019, 19 pages.
Third Party Observations for Japanese Application No. 2016-530611, dated Nov. 1, 2017, with English Translation, 2 pages.
English translation of Japanese Office Action for Japanese Application No. 2016-530610, dated Apr. 24, 2018, 9 pages.
Decision of Refusal received in Japanese Application No. 2016-530610, dated Nov. 28, 2018, (16 pages).

SWEETNER COMPOSITIONS

CROSS-REFERENCE TO RELATED APPLICATIONS

This is the national phase of International Application No. PCT/GB2014/052344, filed 31 Jul. 2014, which claims priority from U.S. Provisional Application No. 61/861,726, filed 2 Aug. 2013. The disclosures of each of these applications are incorporated herein by reference in their entirety for all purposes.

FIELD OF THE INVENTION

The present invention relates to improving the taste of sweeteners and products sweetened with the same. In particular, the present invention relates to the use of anti-foaming agents and flavour enhancers to improve the taste of sweeteners and provide a more sugar-like temporal profile by reducing the delay in sweetness onset and/or reducing the sweetness linger of the sweetener. The present invention further relates to a composition and products comprising the combination of an anti-foaming agent, a flavour enhancer and a sweetener having a beneficial temporal profile.

BACKGROUND OF THE INVENTION

Although desirable in terms of taste, excess intake of high calorie sugars, such as sucrose (table sugar), has long been associated with an increase in diet-related health issues, such as obesity. This worrying trend has caused consumers to become increasingly aware of the importance of adopting a healthier lifestyle and reducing the level of high calorie sugars in their diet.

In recent years, there has been a movement towards the development of substitutes for high calorie sugars, with a particular focus on the development of low or zero-calorie sweeteners. An ideal replacement for a high calorie sugar would be a sweetener that has the same desirable taste characteristics, feel and temporal profile as sucrose, but which also has low or no calories. Aiming to meet this growing need, the market has been flooded with possible candidates for a sugar replacement. Unfortunately, however, many of the low or zero calorie sugar substitutes offered on the market lack one or all of the necessary characteristics, and often exhibit bitterness or off-taste. Therefore, many of the proposed sugar substitutes available are not an ideal replacement for high calorie sugars.

An alternative solution to the replacement of all high calorie sugars in certain food products is the blending of high calorie sugars with a low or zero-calorie sweetener. These blends allow for the reduction in the amount of high calorie sugars that need to be used in a food product, while retaining the same level of sweetness. It has also been found that such blends can work even when the amount of the low or zero-calorie sweetener is used below the level at which it would provide a sweet taste when it is given alone. Similarly to low or zero calorie sugar substitutes, these blends can suffer from the problem of having a bitter or off-taste in comparison to high calorie sugars.

The present invention seeks to provide an improved sweetener composition that can be used in a variety of products and overcomes the temporal profile issues discussed above.

SUMMARY OF THE INVENTION

A first aspect of the invention provides a sweetener composition comprising at least one sweetener, at least one anti-foaming agent, and at least one flavour enhancer, wherein the flavour enhancer is at least one high potency sweetener that contains hydrophilic and hydrophobic structural moieties, and is used in an amount below its sweetness threshold.

In embodiments of the invention, the flavour enhancer is selected from a natural high potency sweetener, a synthetic high-potency sweetener that is a glycoside or a synthetic high-potency sweetener that is derived from an amino acid.

In embodiments of the invention, the at least one sweetener in the sweetener composition is selected from the group consisting of a nutritive sweetener, aspartame, acesulfame, cyclamate, saccharin and sucralose; and salts and/or solvates thereof. For example, at least one sweetener in the sweetener composition may be one or more selected from the group consisting of a 3- to 12-carbon sugar alcohol (e.g. allose, deoxyribose, erythrulose, galactose, gulose, idose, lyxose, mannose, ribose, tagatose, talose, xylose, erythrose, fuculose, gentiobiose, gentiobiulose, isomaltose, isomaltulose, kojibiose, lactulose, altrose, laminaribiose, arabinose, leucrose, fucose, rhamnose, sorbose, maltulose, mannobiose, mannosucrose, melezitose, melibiose, melibiulose, nigerose, raffinose, rutinose, rutinulose, sophorose, stachyose, threose, trehalose, trehalulose, turanose, xylobiose, glucose-fructose syrup, invert sugar, arabitol, glycerol, hydrogenated starch hydrolysate, isomalt, lactitol, maltitol, mannitol, sorbitol and xylitol; allulose (also known as D-psicose), high fructose corn syrup, glucose, erythritol, fructose and sucrose, aspartame, acesulfame, cyclamate, saccharin and sucralose; and salts and/or solvates thereof.

In further embodiments of the invention, the at least one sweetener in the sweetener composition is selected from the group consisting of sucrose, allulose, fructose, high fructose corn syrup, glucose and erythritol, aspartame, acesulfame, cyclamate, saccharin and sucralose; and salts and/or solvates thereof. For example, the at least one sweetener in the sweetener composition may be selected from the group consisting of fructose, sucrose, acesulfame, cyclamate, saccharin and sucralose; and salts and/or solvates thereof.

In yet further embodiments of the invention, the at least one sweetener in the sweetener composition is selected from the group consisting of aspartame, or more preferably acesulfame, cyclamate, saccharin and, particularly, sucralose; and salts and/or solvates thereof.

In embodiments of the invention, the at least one flavour enhancer in the sweetener composition is selected from the group consisting of alitame, brazzein, curculin, hernandulcin, N—[N-[3-(3-hydroxy-4-methoxyphenyl)propyl]-L-[alpha]-aspartyl]-L-phenylalanine 1-methyl ester, N—[N-[3-(3-hydroxy-4-methoxyphenyl)-3-methylbutyl]-L-[alpha]-aspartyl]-L-phenylalanine 1-methyl ester, mabinlin, N—[N-[3-(3-methoxy-4-hydroxyphenyl)propyl]-L-[alpha]-aspartyl]-L-phenylalanine 1-methyl ester, monellin, phyllodulcin and thaumatin; particularly abrusoside A, aspartame, baiyunoside, cyclocarioside I, glycyphyllin, glycyrrhizic acid, monatin, mukurozioside, osladin, periandrins, phlomisosides, phloridzin, polypodoside A, pterocaryoside A, pterocaryoside B and trilobatin; more particularly an ent-kaurane sweetener (e.g. a *stevia* extract, steviol glycosides, glucosylated steviol glycosides, rubusoside, or a rebaudioside, such as rebaudioside A to F, M, N and X) and a Luo Han Guo extract; and yet more particularly neohesperidin dihydrochalcone and neotame; and salts and/or solvates thereof. As will be appreciated, the at least one sweetener and the at least one flavour enhancer cannot be the same.

In embodiments of the invention, when the at least one sweetener is selected from the group consisting of aspartame, or more preferably acesulfame, cyclamate, saccharin and sucralose, and salts and/or solvates thereof, the composition may further comprise a nutritive sweetener. For example, the nutritive sweetener may be one or more selected from the group consisting of a 3- to 12-carbon sugar alcohol, a monosaccharide and a sweet disaccharide. Particular nutritive sweeteners that may be mentioned in embodiments of the invention include one or more selected from the group consisting of allose, deoxyribose, erythrulose, galactose, gulose, idose, lyxose, mannose, ribose, tagatose, talose, xylose, erythrose, fuculose, gentiobiose, gentiobiulose, isomaltose, isomaltulose, kojibiose, lactulose, altrose, laminaribiose, arabinose, leucrose, fucose, rhamnose, sorbose, maltulose, mannobiose, mannosucrose, melezitose, melibiose, melibiulose, nigerose, raffinose, rutinose, rutinulose, sophorose, stachyose, threose, trehalose, trehalulose, turanose, xylobiose, or more preferably glucose-fructose syrup, invert sugar, arabitol, glycerol, hydrogenated starch hydrolysate, isomalt, lactitol, maltitol, mannitol, sorbitol and xylitol; particularly allulose, high fructose corn syrup, glucose and erythritol; and more particularly fructose and sucrose.

In further embodiments of the invention, when the at least one sweetener comprises at least one nutritive sweetener and at least one high potency sweetener selected from the group consisting of aspartame, acesulfame, cyclamate, saccharin and sucralose, and salts and/or solvates thereof, the ratio of the at least one high potency sweetener to the nutritive sweetener is from about 0.01:1 to about 6.25:1 on a weight to weight basis. For example, the ratio of the at least one high potency sweetener to the nutritive sweetener may be greater than about 0.015:1 and less than or equal to about 2:1, from about 0.02:1 to about 0.5:1 or, particularly, from about 0.025:1 to about 0.25:1 on a weight to weight basis. In particular embodiments of the invention, the ratio of the at least one high potency sweetener to the at least one nutritive sweetener may be about 0.025:1 to about 0.08:1 on a weight to weight basis.

In alternative embodiments of the invention, when the at least one sweetener comprises at least one nutritive sweetener and at least one high potency sweetener selected from the group consisting of aspartame, acesulfame, cyclamate, saccharin and sucralose, and salts and/or solvates thereof, the ratio of the at least one high potency sweetener to the at least one nutritive sweetener is from about 0.01:1 to about 0.1:1 on a weight to weight basis. For example, the ratio of the at least one high potency sweetener to the at least one nutritive sweetener may be greater than about 0.015:1 and less than or equal to about 0.05:1, from about 0.02:1 to about 0.04:1 or, particularly, from about 0.025:1 to about 0.035:1 on a weight to weight basis.

In particular embodiments of the invention, the ratio of the at least one high potency sweetener to the at least one nutritive sweetener may be about 0.03:1 on a weight to weight basis.

In still further embodiments of the invention, the at least one anti-foaming agent comprises one or more selected from the group consisting of mineral oil, odourless light petroleum hydrocarbons, petrolatum, petroleum waxes, synthetic isoparaffinic petroleum hydrocarbons, synthetic petroleum wax, paraffin wax, microcrystalline wax, tallow, oxidized tallow, sulfated tallow, oleomargarine, lard, butter, oxystearin, a fatty acid metal salt, ethylene oxide polymer, copolymer condensates of ethylene oxide and propylene oxide, polyethylene glycol, polypropylene glycol, polyethylene glycol (400) dioleate, sorbitan monostearate, polysorbate 60 (polyoxyethylene (20) sorbitan monostearate), polysorbate 65 (polyoxyethylene (20) sorbitan tristearate), polysorbate (polyoxyethylene (20) sorbitan monooleate), n-butoxypolyoxyethylene polyoxypropylene glycol, polyoxyethylene (600) dioleate, polyoxyethylene (600) monoricinoleate and polyoxyethylene (40) monostearate; particularly lecithin, propylene glycol mono and diesters of fatty acids, propylene glycol alginate and calcium alginate; more particularly a fatty acid (e.g. selected from one or more of the group consisting of decanoic acid, oleic acid, capric acid, caprylic acid, lauric acid, myristic acid, palmitic acid and stearic acid) and an alkyl-substituted silicon dioxide; yet more particularly a fatty acid ester, a vegetable oil (e.g. selected from one or more of the group consisting of corn oil, coconut oil and cottonseed oil), silicon dioxide; and particularly a silicone oil.

In particular embodiments of the invention, the at least one anti-foaming agent comprises polydimethylsiloxane and/or silicon dioxide. In an embodiment of the invention, the at least one anti-foaming agent comprises polydimethylsiloxane. In a further embodiment, the at least one anti-foaming agent comprises silicon dioxide. In yet a further embodiment, the at least one anti-foaming agent comprises polydimethylsiloxane and silicon dioxide.

In embodiments of the invention, the at least one anti-foaming agent has a hydrophilic-lipophilic balance value of less than or equal to 10.

In further embodiments of the invention, the ratio of the at least one flavour enhancer to the at least one anti-foaming agent is from about 0.01:1 to about 100:1 on a weight to weight basis. For example, the ratio of the at least one flavour enhancer to the at least one anti-foaming agent is from about 0.1:1 to about 50:1 on a weight to weight basis. In particular embodiments, the ratio of the at least one flavour enhancer to the at least one anti-foaming agent is from about 0.04:1 to about 40:1 (e.g. about 0.4:1 to about 40:1) on a weight to weight basis. For example, the ratio of the at least one flavour enhancer to the at least one anti-foaming agent is from about 0.5:1 to about 2.5:1 or from about 1:1 to 2:1 on a weight to weight basis. In particular embodiments of the invention, the ratio of the at least one flavour enhancer to the at least one anti-foaming agent may be about 2:1 or about 1.9:1 on a weight to weight basis.

In yet further embodiments of the invention, the ratio of the at least one flavour enhancer to the at least one anti-foaming agent is from about 0.004:1 to about 100:1 on a weight to weight basis. For example, the ratio of the at least one flavour enhancer to the at least one anti-foaming agent is from about 0.008:1 to about 100:1, from about 0.008:1 to about 50:1, from about 0.008:1 to about 40:1, from about 0.01:1 to about 40:1, or from about 0.05:1 to about 40:1 on a weight to weight basis.

In further embodiments of the invention, the sweetener composition can be formulated as a syrup, in powder form, in tablet form, as granules, or as a solution.

A second aspect of the invention provides a sweetener composition comprising a sweetener comprising sucralose; an anti-foaming agent comprising polydimethylsiloxane and/or silicon dioxide; and a flavour enhancer comprising neohesperidin dihydrochalcone and neotame, wherein the flavour enhancer is used in an amount below its sweetness threshold. For example, the anti-foaming agent may be polydimethylsiloxane. Alternatively, the anti-foaming agent may be silicon dioxide. In particular embodiments, the anti-foaming agent comprises polydimethylsiloxane and silicon dioxide.

In embodiments of the second aspect of the present invention, the sweetener composition may further comprise a nutritive sweetener selected from one or more of the group consisting of fructose and sucrose.

In certain embodiments of the second aspect of the present invention, the ratio of the at least one flavour enhancer to the at least one anti-foaming agent is about 0.4:1 or about 0.38:1 on a weight to weight basis. In other embodiments, the ratio of the at least one flavour enhancer to the at least one anti-foaming agent is about 2:1 or about 1.9:1 on a weight to weight basis.

A third aspect of the invention provides a product for human and/or animal consumption, comprising a sweetener composition according to the first aspect and second aspects of the invention.

In embodiments of the third aspect of the invention the product can be a food product, a beverage product, a pharmaceutical product, a nutritional product, a sports product, or a cosmetic product.

For example, when the product is a food product, the food product can be selected from the group consisting of a confectionary product, a dessert product, a cereal product, baked goods, frozen dairy products, meats, dairy products, condiments, snack bars, soups, dressings, mixes, prepared foods, baby foods, diet preparations, syrups, food coatings, dried fruit, sauces, gravies, and jams/jellies. For example, the food product may comprise the sweetener composition of the present invention as a coating or frosting formed on the surface of the product.

Alternatively, when the product is a beverage product, the beverage product can be selected from the group consisting of a carbonated beverage, a non-carbonated beverage, fruit-flavoured beverage, fruit-juice, tea, milk, coffee, and the like.

In embodiments where the product is a beverage product, the beverage product may comprise a nutritive sweetener at a concentration of less than 5000 ppm and/or greater than or equal to 80 ppm.

In further embodiments, the beverage product has an acidic pH. For example the pH may be from about 2.0 to about 6.5.

In a yet further embodiment of the third aspect of the invention, the sweetness onset time and/or sweet taste linger has been shortened relative to a product comprising the sweetener alone.

A fourth aspect of the invention provides a use of at least one anti-foaming agent and at least one flavour enhancer to shorten the sweetness onset time and/or the sweetness linger of at least one sweetener, wherein the flavour enhancer is at least one high potency sweetener that contains hydrophilic and hydrophobic structural moieties and is used in an amount below its sweetness threshold.

For example, in embodiments of this aspect, the flavour enhancer is selected from a natural high-potency sweetener, a synthetic high-potency sweetener that is a glycoside or a synthetic high-potency sweetener that is derived from amino acids; and the flavour enhancer is used in an amount below its sweetness threshold.

A fifth aspect of the invention provides a method of making a sweetener composition according to the first or second aspect of the invention, said method comprising mixing at least one sweetener with at least one anti-foaming agent and at least one flavour enhancer.

In embodiments of the fifth aspect, the mixing of the at least one sweetener with the at least one anti-foaming agent and the at least one flavour enhancer may be accomplished by sequential or concomitant mixing.

DETAILED DESCRIPTION

Figure 1:
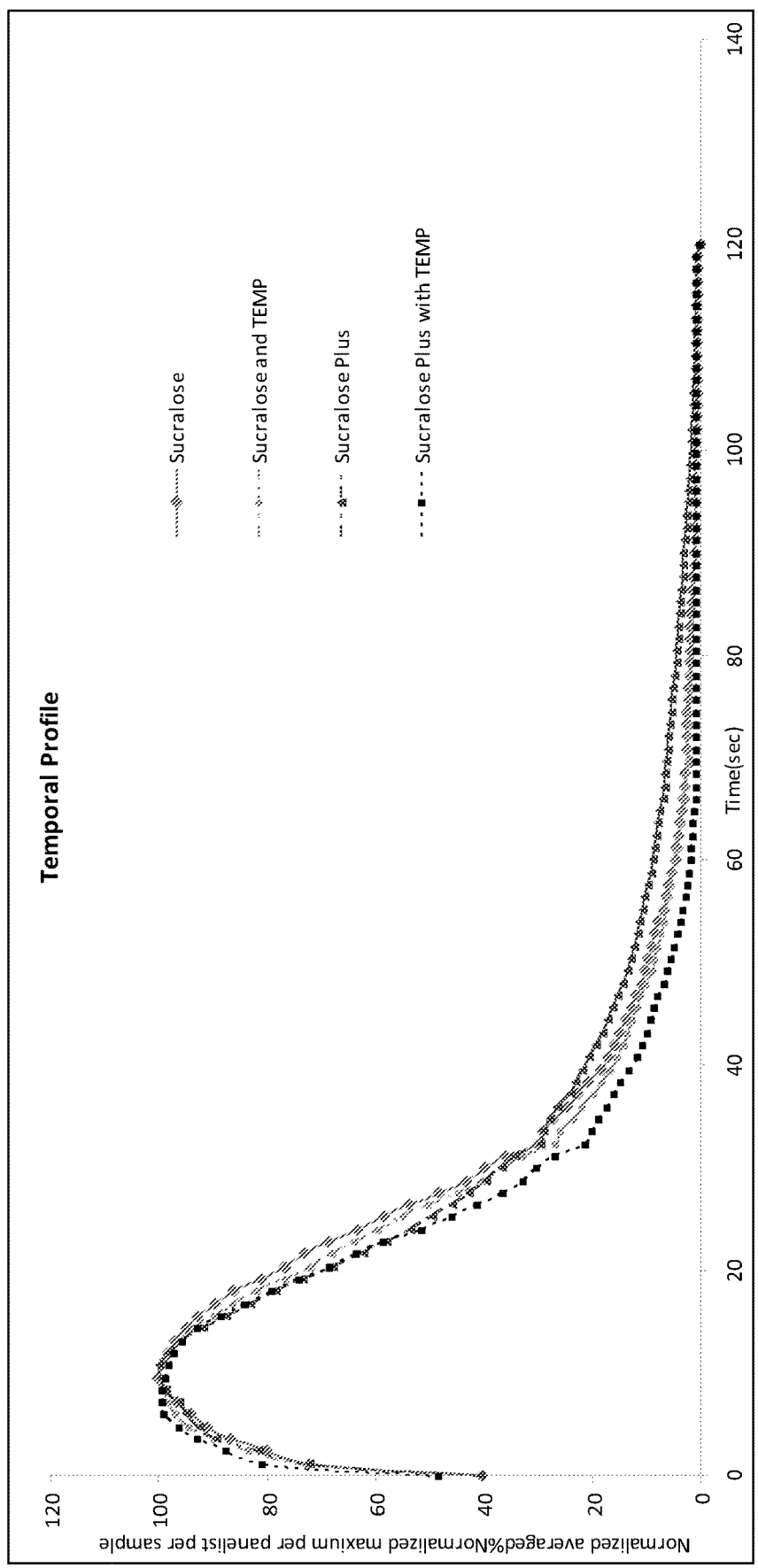
FIG. 1: is a graph showing the temporal profile (over 0 to 120 seconds) of sucralose versus sucralose and TEMP (fructose and MD-20-S FG (a polydimethylsiloxane and silicon dioxide based antifoam)), sucralose plus and sucralose plus with TEMP.
Figure 2:
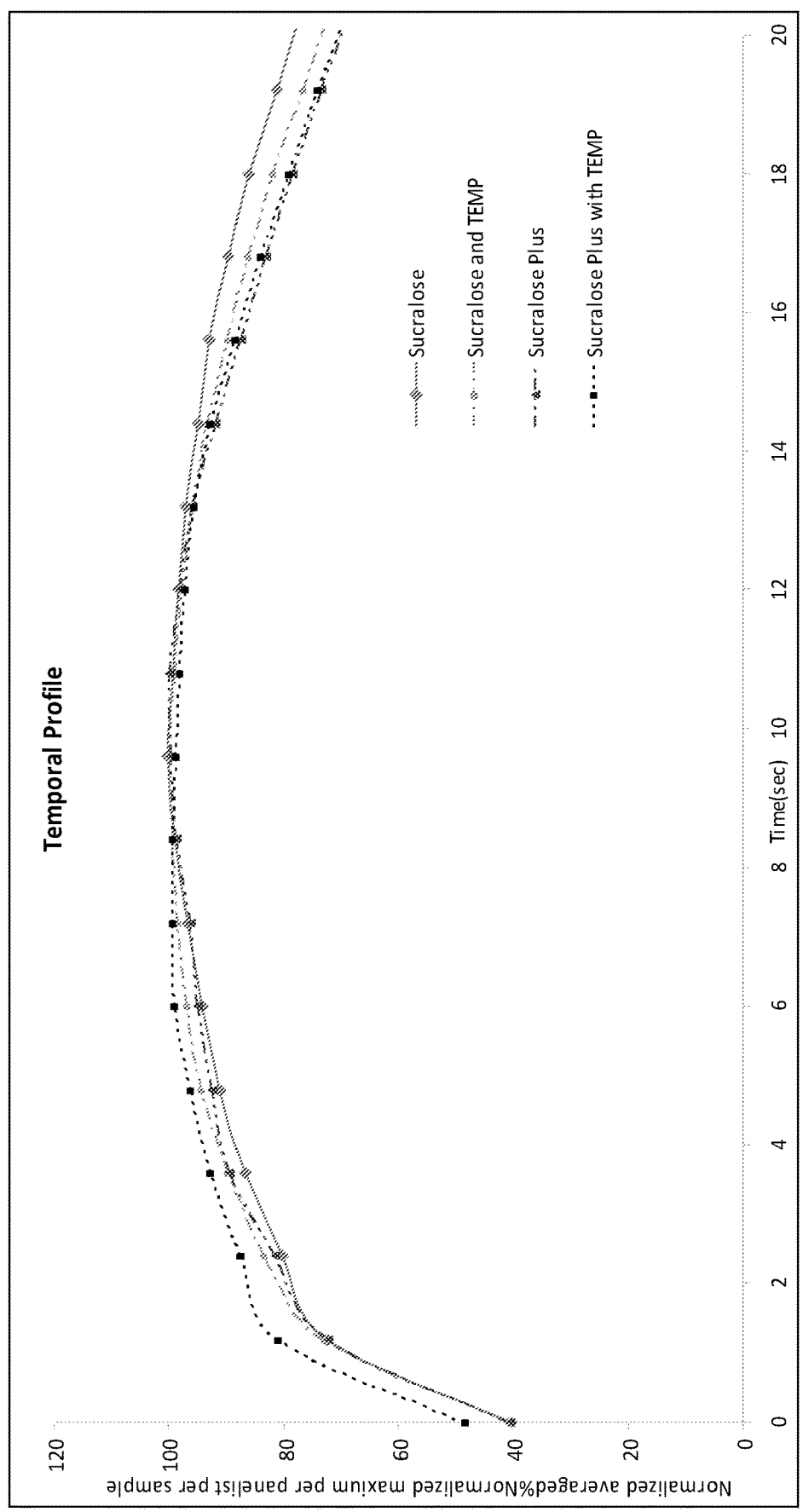
FIG. 2: is a graph showing the temporal profile (over 0 to 20 seconds) of sucralose versus sucralose and TEMP (fructose and MD-20-S FG), sucralose plus and sucralose plus with TEMP.
Figure 3:
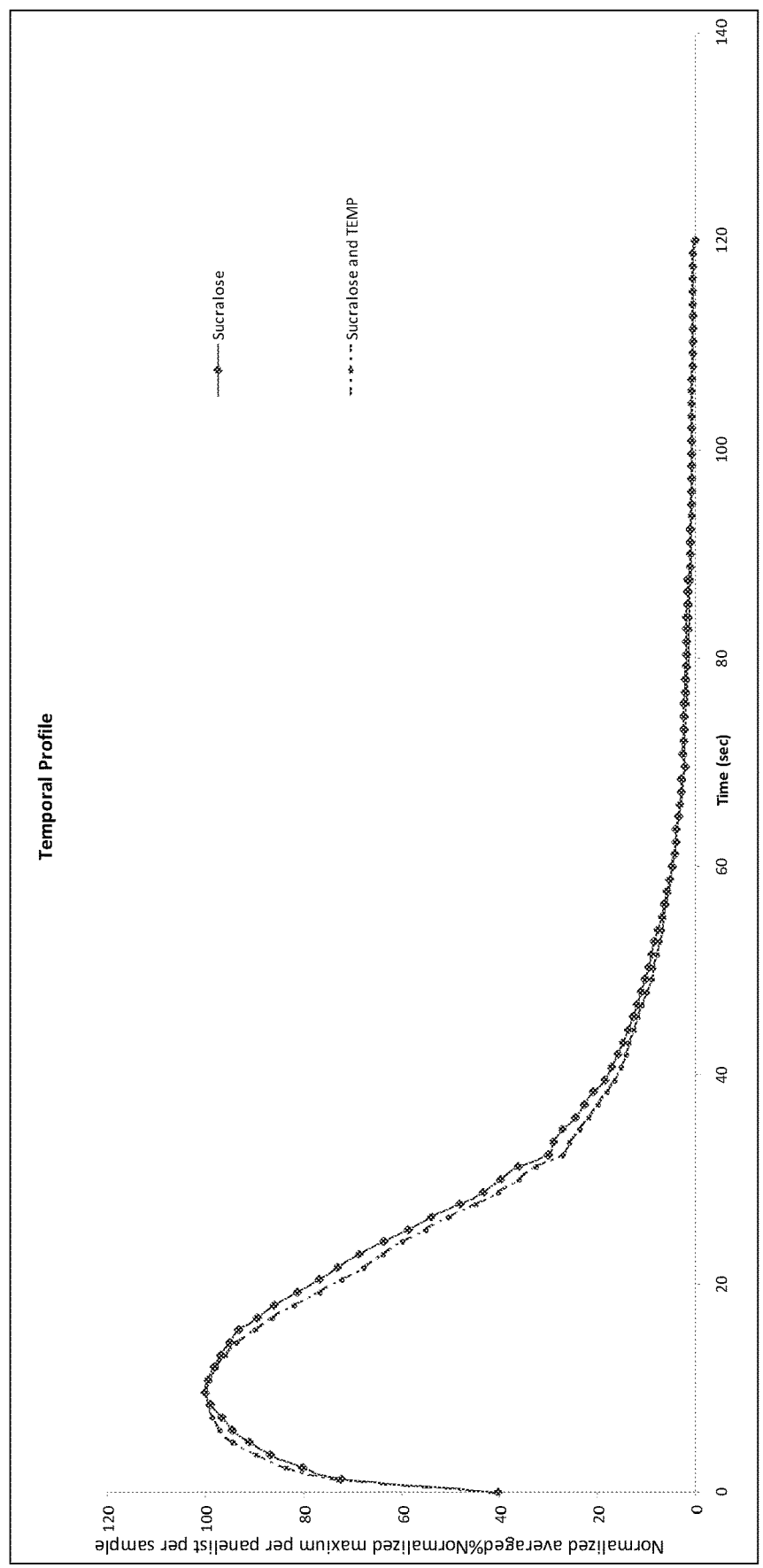
FIG. 3: is a graph showing the temporal profile (over 0 to 120 seconds) of sucralose versus sucralose and TEMP (fructose and MD-20-S FG).
Figure 4:
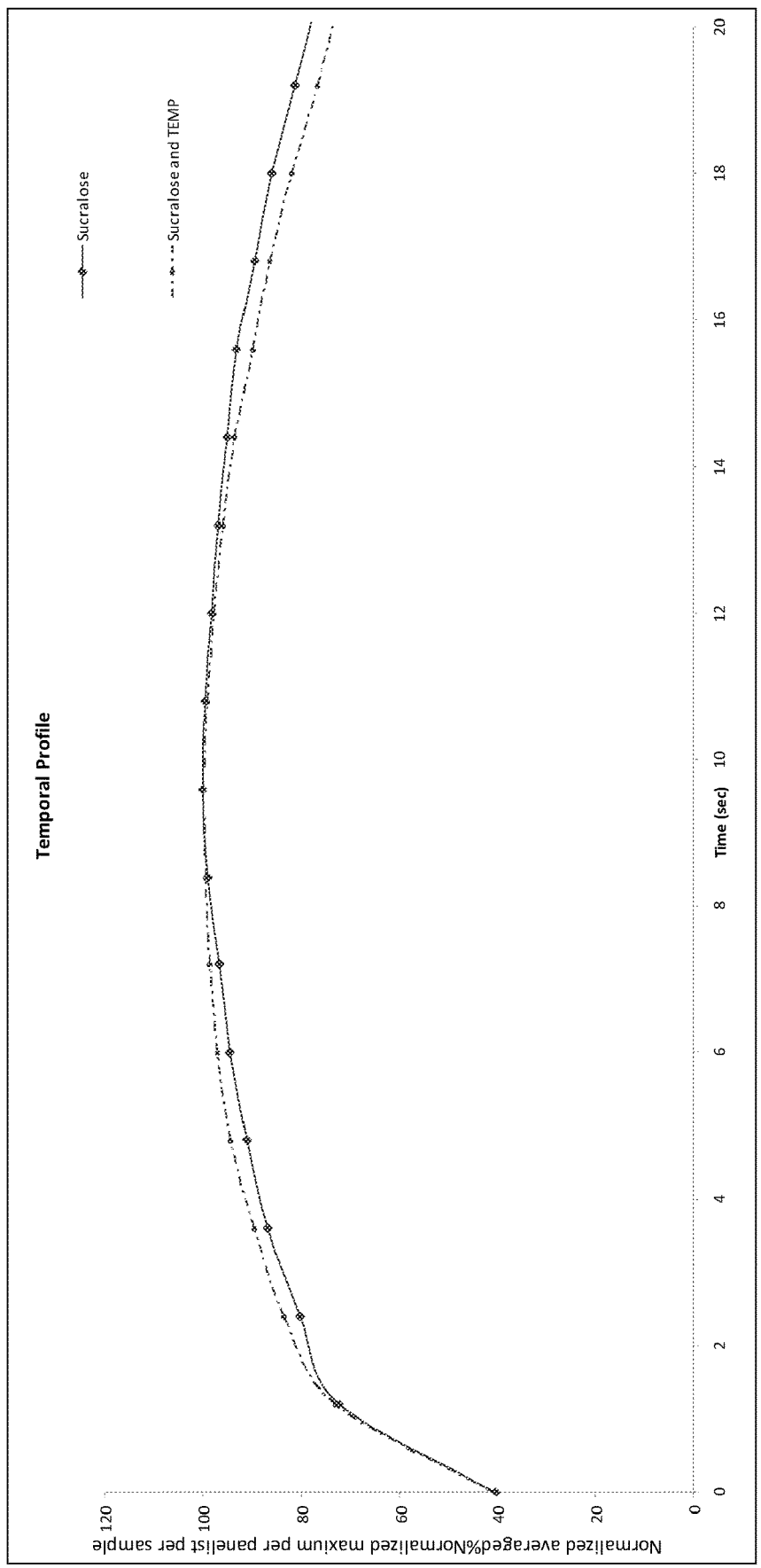
FIG. 4: is a graph showing the temporal profile (over 0 to 20 seconds) of sucralose versus sucralose and TEMP (fructose and MD-20-S FG).
Figure 5:
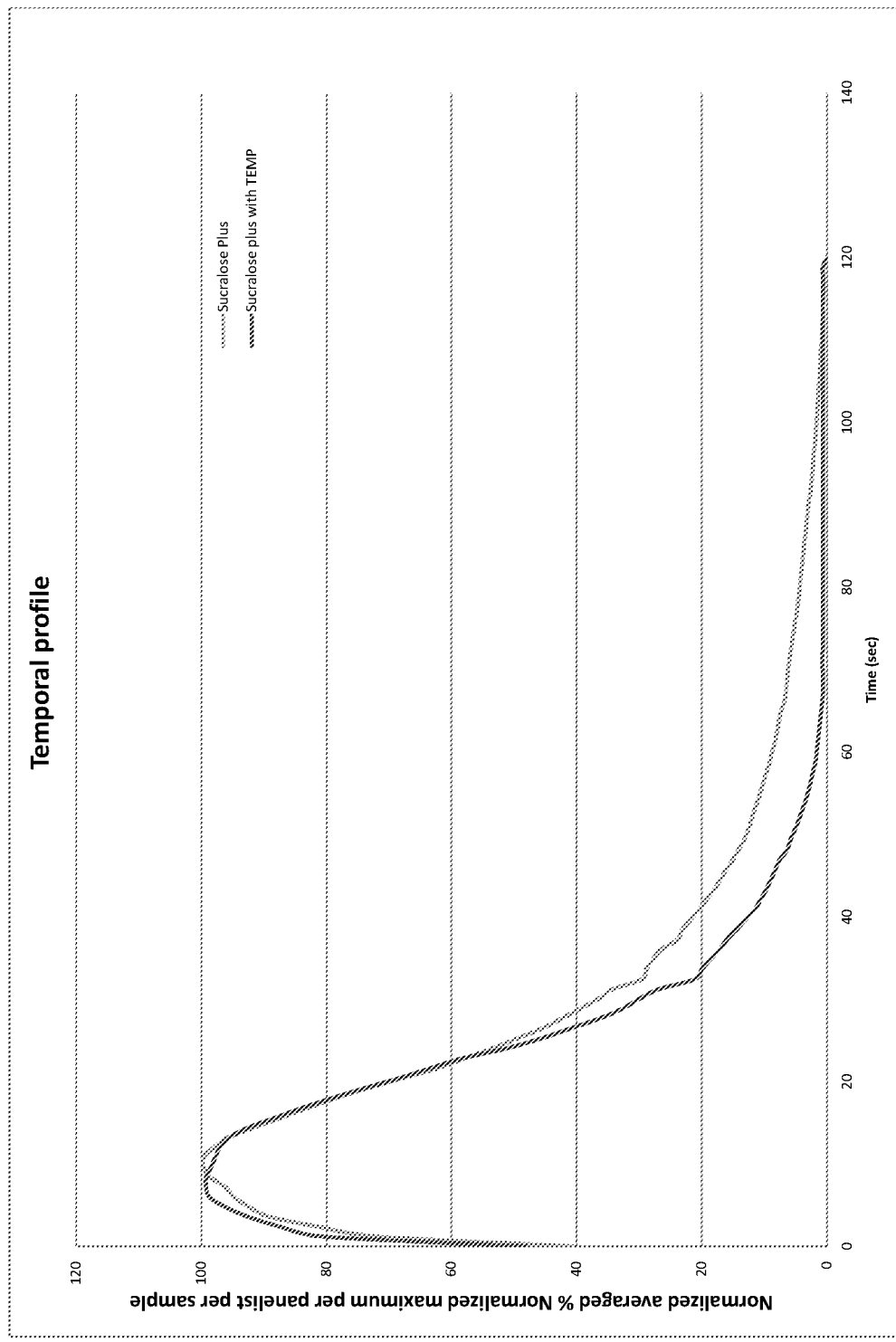
FIG. 5: is a graph showing the temporal profile (over 0 to 120 seconds) of sucralose plus versus sucralose plus with TEMP (fructose and MD-20-S FG).
Figure 6:
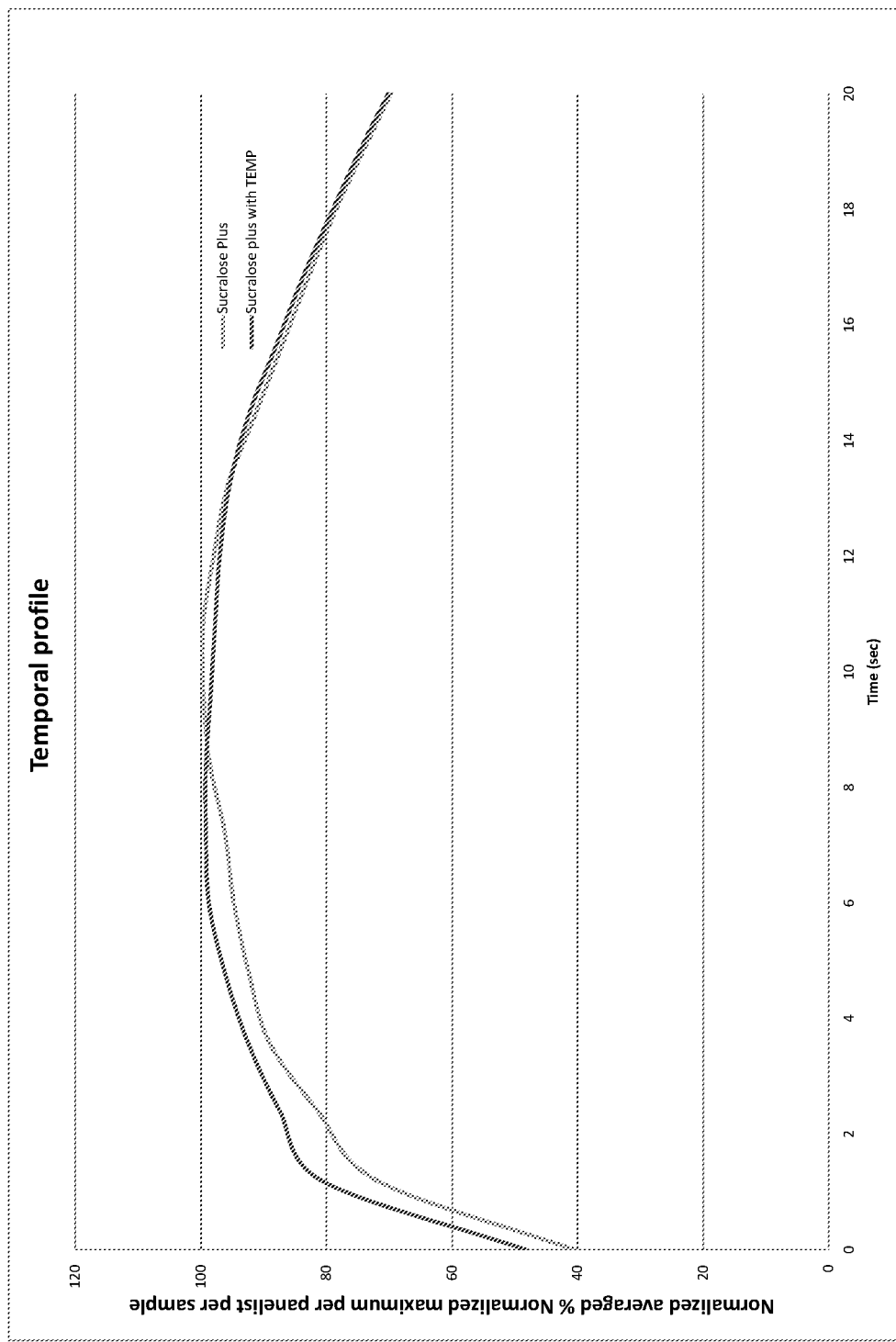
FIG. 6: is a graph showing the temporal profile (over 0 to 20 seconds) of sucralose plus versus sucralose plus with TEMP (fructose and MD-20-S FG).

The present invention is based on the surprising finding that an anti-foaming agent can enhance the sweetness and/or flavour of a sweetener that is used in combination with a flavour enhancer. That is to say, a composition or product containing an anti-foaming agent, a flavour enhancer and a sweetener has an improved taste compared to the same composition or product without the inclusion of the anti-foaming agent.

Additionally, the present invention also discloses the surprising finding that an anti-foaming agent and a flavour enhancer can enhance the sweetness and/or flavour of a sweetener selected from one or more consisting of aspartame, or more preferably acesulfame, cyclamate, saccharin and, particularly, sucralose. That is to say, a composition or product containing an anti-foaming agent, a flavour enhancer and the sweeteners defined above has an improved taste compared to the same composition or product without the inclusion of the anti-foaming agent and flavour enhancer.

Furthermore, it has been found that the inclusion of an anti-foaming agent in the aforementioned compositions or products addresses problems that may be associated with the sweeteners alone or in combination with the flavour enhancer, in particular, with regard to metallic taste and/or undesirable temporal profile. Thus, the sweetener composition of the present invention and products containing it improve the balance of flavor by reducing off-taste, and may provide a more desirable temporal profile.

In addition, the sweetener composition of the present invention and products containing it will generally be lower in calories compared to equivalent compositions and products sweetened with sucrose or fructose (e.g. high-fructose corn syrup).

The term "temporal profile" as used herein, is a measure of perceived sweetness intensity over time. A desirable or advantageous temporal profile is one wherein sweetness is observed quickly and has a short linger similar to that of sucrose.

Benefits that may be associated with embodiments of the present invention include better overall acceptability, better mouthfeel, reduced off-taste and a desirable temporal profile, as well as being cost effective.

In general terms, the present invention relates to a sweetener composition comprising:
  at least one sweetener;
  at least one anti-foaming agent; and
  at least one flavour enhancer, wherein:
    the flavour enhancer is:
      at least one high potency sweetener that contains hydrophilic and hydrophobic structural moieties; and
      used in an amount below its sweetness threshold.

The term "sweetener" as used herein refers to a substance that provides a sweet taste. In other words, the sweetener is a nutritive sweetener or a non-nutritive sweetener. However, in particular embodiments, the sweetener does not contain a sugar or a sugar alcohol. In other words, in particular embodiments, the sweetener is a non-nutritive sweetener.

The term "high potency sweetener contains hydrophilic and hydrophobic structural moieties" as used herein refers to a high potency sweetener that has an amphiphilic structure. Examples of high potency sweeteners that may be mentioned herein include those selected from the group consisting of a natural high potency sweetener, a synthetic high potency sweetener that is a glycoside, or a synthetic high potency sweetener that is derived from an amino acid.

The term "non-nutritive sweetener" as used herein refers to a sweetener that offers little to no calories when ingested.

The term "nutritive sweetener" as used herein refers to a sweetener that contains carbohydrate and provides energy. Nutritive sweeteners may be further classified into monosaccharides or disaccharides, which impart 4 kcal/g, or sugar alcohols (polyols), which provide an average of 2 kcal/g, as discussed in "*Position of the American Dietetic Association: Use of nutritive and nonnutritive sweeteners*" *J. Am. Diet Assoc.* 2004; 104(2):255-275.

In an embodiment, the nutritive sweetener is one or more selected from the group consisting of a 3- to 12-carbon sugar alcohol, a monosaccharide and a sweet disaccharide. For example, in embodiments of the invention, the nutritive sweetener may be one or more selected from the group consisting of allose, deoxyribose, erythrulose, galactose, gulose, idose, lyxose, mannose, ribose, tagatose, talose, xylose, erythrose, fuculose, gentiobiose, gentiobiulose, isomaltose, isomaltulose, kojibiose, lactulose, altrose, laminaribiose, arabinose, leucrose, fucose, rhamnose, sorbose, maltulose, mannobiose, mannosucrose, melezitose, melibiose, melibiulose, nigerose, raffinose, rutinose, rutinulose, sophorose, stachyose, threose, trehalose, trehalulose, turanose, xylobiose, or more particularly, sucrose, fructose, glucose, glucose-fructose syrup, high fructose corn syrup, invert sugar, allulose (also known as D-psicose), arabitol, erythritol, glycerol, hydrogenated starch hydrolysate, isomalt, lactitol, maltitol, mannitol, sorbitol and xylitol.

In an alternative embodiment, the nutritive sweetener is one or more selected from the group consisting of sucrose, fructose, allulose (also known as D-psicose), high fructose corn syrup, glucose and erythritol.

In a preferred embodiment, the nutritive sweetener is fructose and/or sucrose. For example, the nutritive sweetener may be fructose. Alternatively, the nutritive sweetener may be sucrose. In certain embodiments, the nutritive sweetener is fructose and sucrose.

Sweeteners that may be mentioned in certain embodiments of the invention include a nutritive sweetener, aspartame, cyclamate, saccharin and sucralose, and salts and/or solvates thereof. For example, the sweetener composition may be selected from the group consisting of a 3- to 12-carbon sugar alcohol (e.g. allose, deoxyribose, erythrulose, galactose, gulose, idose, lyxose, mannose, ribose, tagatose, talose, xylose, erythrose, fuculose, gentiobiose, gentiobiulose, isomaltose, isomaltulose, kojibiose, lactulose, altrose, laminaribiose, arabinose, leucrose, fucose, rhamnose, sorbose, maltulose, mannobiose, mannosucrose, melezitose, melibiose, melibiulose, nigerose, raffinose, rutinose, rutinulose, sophorose, stachyose, threose, trehalose, trehalulose, turanose, xylobiose, glucose-fructose syrup, invert sugar, arabitol, glycerol, hydrogenated starch hydrolysate, isomalt, lactitol, maltitol, mannitol, sorbitol and xylitol; allulose (also known as D-psicose), high fructose corn syrup, glucose, erythritol, fructose and sucrose), aspartame, acesulfame, cyclamate, saccharin and sucralose; and salts and/or solvates thereof. Particular sweeteners that may be mentioned in certain embodiments of the invention include acesulfame, cyclamate, saccharin and sucralose, and salts and/or solvates thereof.

The term "sweetness threshold" as used herein is the maximum concentration of a sweetener that is not perceived as sweet on its own. In respect of food and beverage products, the use of a sweetener at below its sweetness threshold is generally referred to as using the sweetener at a flavour level. In other words, the sweetener contributes to improving the overall sweetness and/or flavour of a food or beverage product, but does it while in an amount that would not provoke any sweet taste in a subject if given without the other ingredients of said food or beverage product.

The term "natural high potency sweetener" as used herein refers to a high potency sweetener obtained from a natural source. For example, a natural high potency sweetener may be used in its raw form (e.g. as a plant) or may be extracted or purified from the natural source. Natural high potency sweeteners that may be mentioned in certain embodiments of the invention include abrusoside A, baiyunoside, brazzein, curculin, cyclocarioside I, glycyphyllin, glycyrrhizic acid, hernandulcin, a Luo Han Guo extract, mabinlin, monatin, monellin, mukurozioside, osladin, periandrins, phlomisosides, phloridzin, phyllodulcin, polypodoside A, pterocaryoside A, pterocaryoside B, rubusoside, a *stevia* extract (e.g. steviol glycosides, or particularly a rebaudioside, such as rebaudioside A to F, M, N and X), thaumatin and trilobatin, and salts and/or solvates thereof.

The term "synthetic high potency sweetener" as used herein refers to a high potency sweetener that has been produced using one or more synthetic steps. Synthetic high potency sweeteners that may be mentioned in certain embodiments of the invention include alitame, aspartame, a glucosylated steviol glycoside, N—[N-[3-(3-hydroxy-4-methoxyphenyl)propyl]-L-[alpha]-aspartyl]-L-phenylalanine 1-methyl ester, N—[N-[3-(3-hydroxy-4-methoxyphenyl)-3-methylbutyl]-L-[alpha]-aspartyl]-L-phenylalanine 1-methyl ester, N—[N-[3-(3-methoxy-4-hydroxyphenyl)propyl]-L-[alpha]-aspartyl]-L-phenylalanine 1-methyl ester neohesperidin dihydrochalcone, and neotame, and salts and/or solvates thereof.

The term "high-potency sweetener that is a glycoside" or "glycoside-derived high potency sweeteners" as used herein refers to a high potency sweetener that is a molecule in which a sugar is bound to an organic moiety that is not itself a sugar. High-potency sweeteners that are glycosides that may be mentioned in certain embodiments of this invention include abrusoside A, baiyunoside, cyclocarioside I, dulcoside A, dulcoside B, glycyphyllin, glycyrrhizic acid, a glucosylated steviol glycoside, mogrosides (e.g. mogroside IV, mogroside V), mukurozioside, neomogroside, osladin, periandrins, phlomisosides, phloridzin, polypodoside A, pterocaryoside A, pterocaryoside B, a rebaudioside (e.g. rebaudioside A, rebaudioside B, rebaudioside C, rebaudioside D, rebaudioside E, rebaudioside F, rebaudioside M, rebaudioside N, rebaudioside X), rubusoside, siamenoside, *stevia*, stevioside, trilobatin and neohesperidin dihydrochalcone.

The term "high potency sweetener that is derived from an amino acid" or "amino acid-derived high potency sweetener" as used herein refers to high potency sweetener that contains at least one amino acid as part of its molecular structure. High potency sweeteners that are derived from an amino acid and that may be mentioned in certain embodiments of this invention include monatin (e.g. monatin, monatin SS, monatin RR, monatin RS, monatin SR), N—[N-[3-(3-hydroxy-4-methoxyphenyl)propyl]-L-[alpha]-aspartyl]-L-phenylalanine 1-methyl ester, N—[N-[3-(3-hydroxy-4-methoxyphenyl)-3-methylbutyl]-L-[alpha]-aspartyl]-L-phenylalanine 1-methyl ester and N—[N-[3-(3-methoxy-4-hydroxyphenyl)propyl]-L-[alpha]-aspartyl]-L-phenylalanine 1-methyl ester, and salts and/or solvates thereof.

The term "Monk Fruit extract" or "Luo Han Guo extract" as used herein refers to an extract or sample taken from a Monk Fruit from the Monk Fruit plant (i.e. a Luo Han Guo fruit from a Luo Han Guo plant), *Siraitia grosvenorii*, comprising at least one mogroside. The term "mogroside composition" as used herein refers to a composition comprising at least one mogroside.

The term "mogroside" as used herein refers to a family of compounds found in plants such as Monk Fruit, also known as Luo Han Guo. Mogrosides are glycosides of cucurbitane derivatives.

Mogroside V (also known as esgoside) has the following formula:

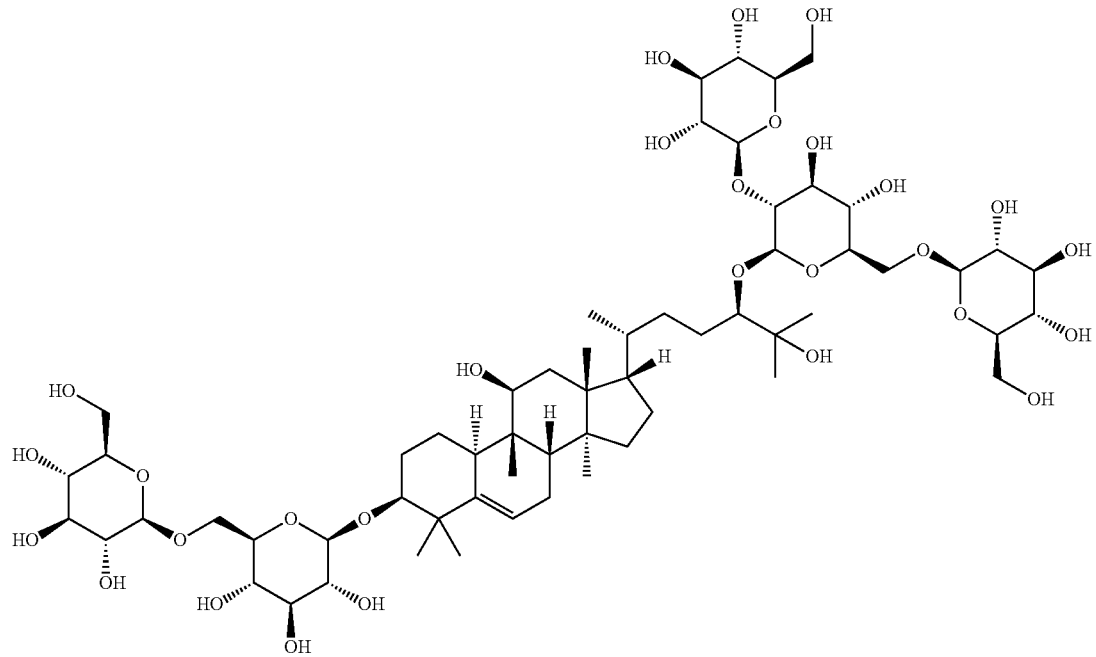

Mogroside IV has the following formula:

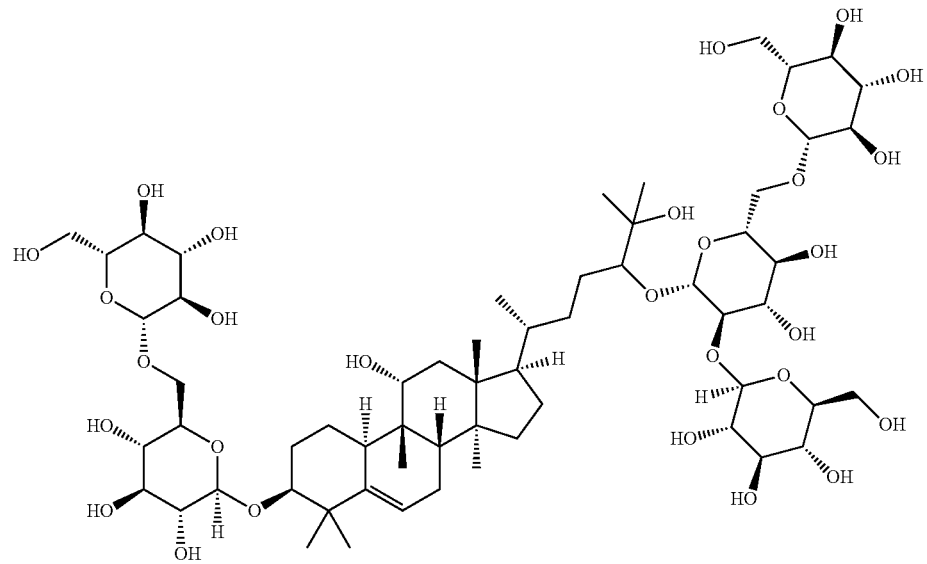

11-Oxomogroside V has the following formula:
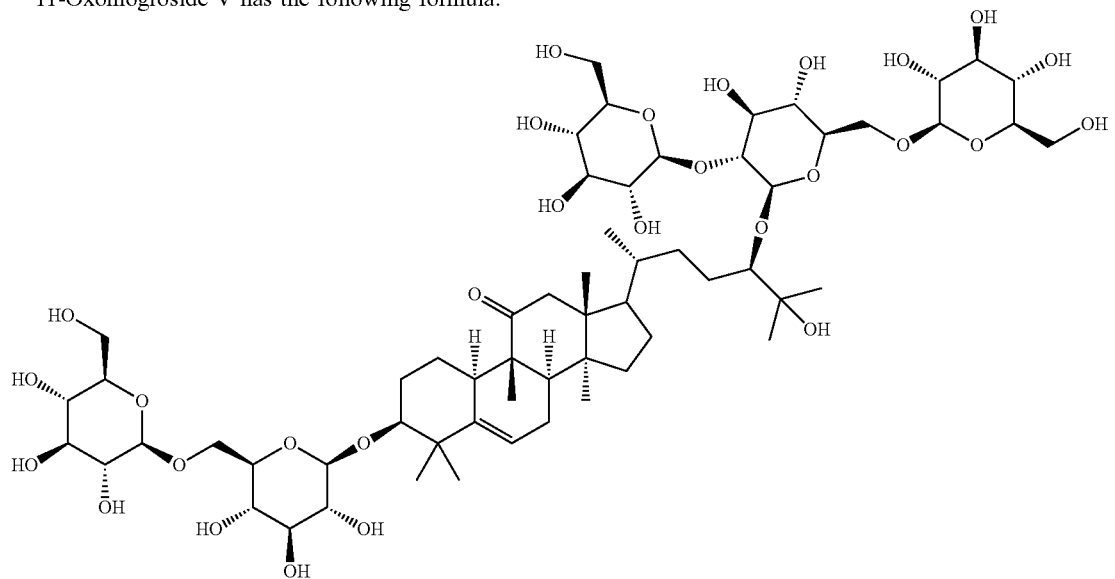
Siamenoside I has the following formula:
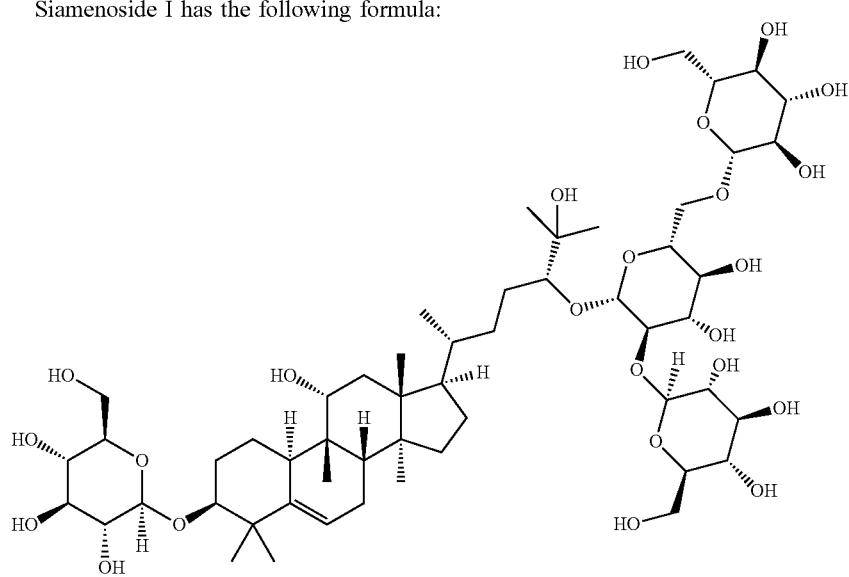
Mogroside VI has the following formula:
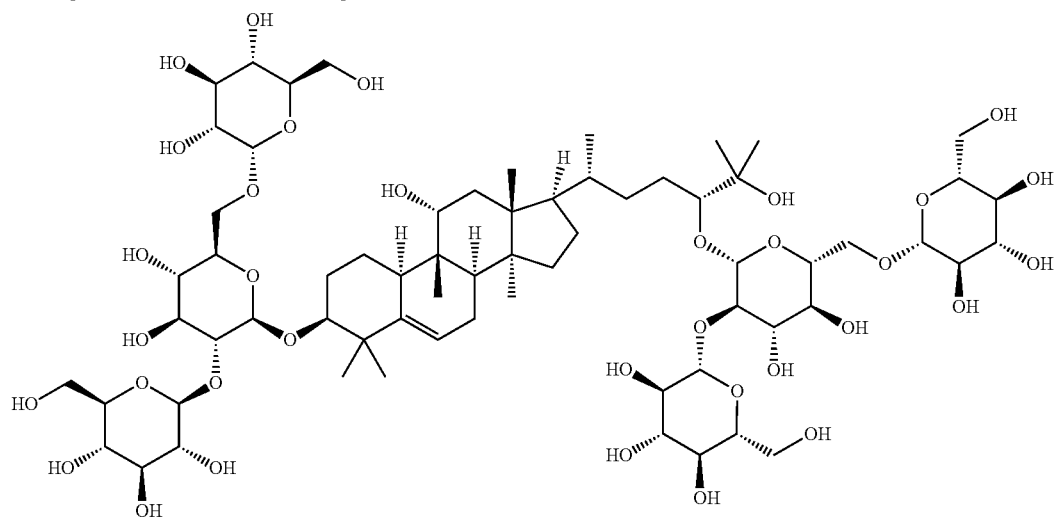

Mogroside III E has the following formula:

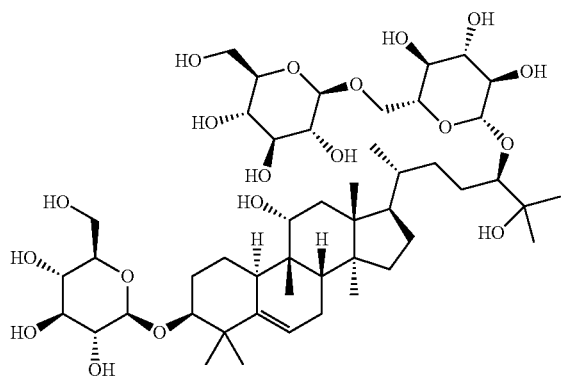

Further mogrosides include neomogroside.

In an embodiment, the mogroside is selected from the group consisting of mogroside V, mogroside IV, mogroside VI, oxomogroside V (e.g. 11-oxomogroside V), mogroside IIIE, neomogroside and siamenoside I or mixtures thereof. It is generally preferred that at least four mogrosides are present in the sweetener composition namely, mogroside V, mogroside IV, 11-oxomogroside V and siamenoside I. It is particularly preferred that the at least one mogroside is mogroside V.

In a further preferred embodiment, the at least one mogroside is from a fruit from a plant of the Cucurbitaceae family. The Cucurbitaceae family of plants includes the plant species *Siraitia grosvenorrii*, which is also known as the Monk Fruit plant. The mogroside may be present in the sweetener composition of the present invention in an extract from a fruit of a plant of the Cucurbitaceae family. The fruit extract comprises at least one mogroside. It is particularly preferred that the fruit is the Monk Fruit from the species *Siraitia grosvenorrii*.

The fruit extract or Monk Fruit extract for use in the present invention may be prepared as follows: The fruit is crushed to release its natural juices. The crushed fruit is then infused with hot water to extract the vitamins, antioxidants and sweet components. The infusion is then passed through a series of filters to obtain a pure, sweet fruit concentrate.

In a particularly preferred embodiment, the fruit extract comprises a mogroside composition in an amount of at least about 50% by weight relative to the total weight of the fruit extract. Preferably, the fruit extract comprises a mogroside composition in an amount of about 50% to about 90% by weight relative to the total weight of the fruit extract.

Luo Han Guo extracts are available commercially from a number of sources. Methods of producing such extracts are described in U.S. Pat. No. 5,411,755 and U.S. Publication No. 2006/0003053, both incorporated herein by reference for all useful purposes. Typically, mogroside V is the most abundant single mogroside component of Luo Han Guo extracts, accompanied by other mogrosides such as mogrosides I, II, III, IV and VI as well as other extracted materials, such as polyphenols, flavonoids, melanoidins, terpenes, proteins, sugars, aromatic glycosides, and semi-volatile organic compounds. In some embodiments of the invention, the mogroside V is provided in the form of a Luo Han Guo extract (either raw or purified and/or concentrated to increase mogroside V content).

In a preferred embodiment, the mogroside composition comprises at least one mogroside selected from the group consisting of mogroside V, mogroside IV, mogroside VI, oxomogroside V (e.g. 11-oxomogroside V), mogroside IIIE and siamenoside I or mixtures thereof. It is generally preferred that at least four mogrosides are present in the mogroside composition, namely, mogroside V, mogroside IV, 11-oxomogroside V and siamenoside I.

It is particularly preferred that the fruit extract comprises about 40% to about 65% by weight of mogroside V and about 0% to about 30% by weight of mogroside IV, mogroside VI, oxomogroside V (e.g. 11-oxomogroside V), mogroside IIIE or siamenoside I, or mixtures thereof.

In a further embodiment, the fruit extract comprises about 50% to about 60% by weight of mogroside V and about 0% to about 30% by weight of mogroside IV, mogroside VI, oxomogroside V (e.g. 11-oxomogroside V), mogroside IIIE or siamenoside I, or mixtures thereof.

In alternative embodiments, mogroside V constitutes at least 40 wt % of the extract, or at least 45 wt %, or at least 50 wt %. Typically, mogroside V will constitute at most 95 wt % of the extract, at most 85 wt % of the extract, at most 75 wt % of the extract, at most 70 wt % of the extract, or at most 65 wt %, or at most 60 wt %.

For example, the Luo Han Guo extract may be one of the Luo Han Guo extracts described in US 2012/0264831, the entire content of which is incorporated herein by reference. In particular, the Luo Han Guo extract and blend disclosed in Examples 1 and 5, respectively, of US 2012/0264831 are incorporated herein by reference.

Commercially available Luo Han Guo powdered fruit extract (e.g. as obtained following the methods of producing such extracts described in U.S. Pat. No. 5,411,755 and U.S. Publication. No. 2006/0003053), typically containing at least 40% of Mogroside V (d.s.b), may be treated with activated carbon as follows. Dry extract is dissolved in deionized water at a concentration of at least about 1 wt %, and typically at most about 70 wt %. The water is heated to a temperature sufficient to favour the dissolution of the powdered material, typically in a range between ambient temperature and 71.1° C., and optionally filtered using a microfiltration membrane or using filtration paper with a non-reactive filtration aid. The purpose of the microfiltration is to remove insoluble proteins and/or microorganisms that could deteriorate the product. The resulting filtrate is subjected to adsorption with active carbon (also known as activated carbon). The carbon may be any form of active carbon available, and may for example be derived from wood, bituminous coal, lignite coal, coconut, bone char, or any other source. In one embodiment, the active carbon is obtained by steam activation of carbon from lignite coal. Typically, the carbon is in the form of granules, but other physical forms such as powders or bead activated carbon may also be employed. It will generally be advantageous to utilize an active carbon which is highly porous and which has a high surface area (e.g., over 100 $m^2/g$, over 200 $m^2/g$, or over 300 $m^2/g$). The non-desirable components causing the off-taste (as well as other undesirable substances such as pesticides) are adsorbed to the carbon, but the improved taste material is not adsorbed and is continuously eluted. The method allows for recovery yields (dry substance basis) between 50% and 99.9%. The amount of active carbon used may vary from 0.05% to 150% (as a percentage of the dry substance present in the aqueous solution of Luo Han Guo fruit extract). More typically, to achieve sufficiently low levels of off-taste components, at least 2 wt % or at least 5 wt % of activated carbon relative to Luo Han Guo fruit extract is used on a solids basis. Preferably, at least 6 wt % or at least 10 wt % of activated carbon relative to Luo Han Guo fruit extract gives the best results. Typically, at most 15 wt % will be used.

The term "an ent-kaurane sweetener" as used herein refers to any high potency sweetener that contains a core structure that is derived from ent-kaurane. In an embodiment, the ent-kaurane sweetener may be a *stevia* extract, one or more glucosylated steviol glycosides, or one or more steviol glycosides. In further embodiments, the ent-kaurane sweetener may be rubusoside or a rebaudioside (e.g. rebaudioside A to F, M, N and X).

The term "*stevia* extract" as used herein refers to an extract or sample taken from a *Stevia* plant, *Stevia rebaudiana*, comprising at least one steviol glycoside. The term "steviol glycoside" means any of a number of naturally occurring compounds with a general structure of the steviol diterpene ring system with one or more saccharide residues chemically attached to the ring. In the present specification, the terms "*stevia* extract" and "steviol glycosides" may be used interchangeably.

Steviol glycosides that may be extracted from *Stevia* include the six rebaudiosides (i.e., rebaudioside A to F, M, N and X), rubusoside, stevioside (the predominant glycoside in extracts from wild type *Stevia*), and dulcosides. Any of said steviol glycosides may be used in embodiments of the invention.

The *stevia* extract that may be used in the present invention preferably comprises steviol glycosides in a total amount of at least 90 weight %, preferably in a total amount of 95 weight % or more, relative to the total weight of the *stevia* extract on a dry solids basis. For example, the *stevia* extract may comprise steviol glycosides in a total amount of at least 90, 91, 92, 93, 94, 95, 96, 97, 98 or 99 weight %, relative to the total weight of the *stevia* extract on a dry solids basis.

In particular embodiments of the invention, when a *stevia* extract is used, the extract preferably contains rebaudioside A and rebaudioside B. For example, the *stevia* extract may comprise Rebaudioside A in an amount of from about 60 weight % to about 85 weight %, preferably from about 70 weight % to about 85 weight %, and more preferably from about 75 weight % to about 80 weight %, relative to the combined total weight of steviol glycosides in the *stevia* extract on a dry solids basis. In some embodiments, the *stevia* extract comprises Rebaudioside A in an amount of from about 60 weight % to about 80 weight %, preferably from about 67 weight % to about 73 weight %, relative to the combined total weight of steviol glycosides in the *stevia* extract on a dry solids basis. For example, the *stevia* extract may comprise Rebaudioside A in an amount of 60, 61, 62, 63, 64, 65, 66, 67, 68, 69, 70, 71, 72, 73, 74, 75, 76, 77, 78, 79, 80, 81, 82, 83, 84 or 85 weight %, relative to the combined total weight of steviol glycosides in the *stevia* extract on a dry solids basis.

In preferred embodiments, the *stevia* extract comprises Rebaudioside B in an amount of from about 15 weight % to about 30 weight %, preferably from about 19 weight % to about 23 weight %, relative to the combined total weight of steviol glycosides in the *stevia* extract on a dry solids basis. For example, the *stevia* extract may comprise Rebaudioside B in an amount of 15, 16, 17, 18, 19, 20, 21, 22, 23, 24, 25, 26, 27, 28, 29 or 30 weight %, relative to the combined total weight of steviol glycosides in the *stevia* extract on a dry solids basis.

In further preferred embodiments, the *stevia* extract comprises Rebaudioside A and Stevioside in a combined total amount of at least 70 weight %, preferably in a combined total amount of 75 weight % or more, relative to the total weight of the *stevia* extract on a dry solids basis.

Alternatively, the *stevia* extract may be the *stevia* extracts described in WO 2012/102769, the entire content of which is incorporated herein by reference. A particular *stevia* extract that may be mentioned herein relates to the *stevia* extract described as an embodiment of the invention in Example 1 of WO 2012/102769, and is incorporated herein by reference.

For example, a *stevia* extract that may be mentioned herein may relate to a formulation containing 70.56 wt % rebaudioside A, 6.45 wt % stevioside, 20.97 wt % rebaudioside B and 2.02 wt % rebaudioside C. Alternatively or additionally, a *stevia* extract that may be mentioned herein may relate to a formulation having a concentration of rebaudioside B relative to the total amount of sweet steviol glycosides of about 21% and a ratio of rebaudioside A to rebaudioside B of about 3:1.

It will be appreciated that combinations or blends of various high potency sweeteners may be used. For example, a blend that may be used in embodiments of the invention relates to a blend comprising 75 wt % of a purified Luo Han Guo extract prepared according to the method outlined above with 25 wt % of a *stevia* extract consisting of approximately 75 wt % rebaudioside A and 25 wt % stevioside.

The term "glucosylated steviol glycoside" as used herein refers to α-glucosylated steviol glycosides such that additional glucose moieties (generally one to three additional glucose moieties) are bonded to the original steviol glycoside structure via sterio- and regio-specific 1,4-α-D-glycosidic bonds. Non-limiting examples of a glucosylated steviol glycoside include monoglucosyl rebaudioside B, monoglucosyl stevioside, monoglucosyl rebaudioside C, monoglucosyl rebaudioside A, diglucosyl rebaudioside B, diglucosylstevioside, diglucosyl rebaudioside C, diglucosyl rebaudioside A, triglucosyl rebaudioside B and triglucosyl rebaudioside A.

The term "salts thereof" when used herein refers to acid addition salts and base addition salts. Such salts may be formed by conventional means, for example by reaction of a free acid or a free base form of a sweetener with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a sweetener in the form of a salt with another counter-ion, for example using a suitable ion exchange resin.

Examples of salts that may be mentioned herein include acid addition salts derived from mineral acids and organic acids, and salts derived from metals such as calcium, magnesium, or preferably, potassium and sodium.

Particular examples of salts are salts derived from mineral acids such as hydrochloric, hydrobromic, phosphoric, metaphosphoric, nitric and sulphuric acids; from organic acids, such as tartaric, acetic, citric, malic, lactic, fumaric, benzoic, glycolic, gluconic, succinic, arylsulphonic acids; and from metals such as sodium, magnesium, or preferably, potassium and calcium.

The term "solvates" when used herein refers to the sweeteners and their salts. Solvates that may be mentioned herein are solvates formed by the incorporation into the solid state structure (e.g. crystal structure) of the sweeteners of a non-toxic solvent (referred to below as the solvating solvent). Examples of such solvents include water, alcohols (such as ethanol, isopropanol and butanol) and dimethylsulphoxide. Solvates can be prepared by recrystallising the sweeteners with a solvent or mixture of solvents containing the solvating solvent. Whether or not a solvate has been formed in any given instance can be determined by subjecting crystals of the sweetener to analysis using well known and standard techniques such as thermogravimetric analysis (TGE), differential scanning calorimetry (DSC) and X-ray crystallography.

The solvates can be stoichiometric or non-stoichiometric solvates. Particular solvates that may be mentioned herein are hydrates, and examples of hydrates include hemihydrates, monohydrates and dihydrates.

The term "anti-foaming agent", "defoaming agent" or variations of these terms as used herein refers to an agent that reduces and/or hinders the formation of a foam. That is, an anti-foaming agent may reduce a foam that has already formed or hinder the development of foam. Alternatively, the anti-foaming agent both reduces a foam that has already formed and hinders the formation of any further foam.

In certain embodiments of the invention, the sweetener is not a flavour enhancer.

In further embodiments of the invention, the sweetener may not be a natural high-potency sweetener, a synthetic high-potency sweetener that is a glycoside or a synthetic high-potency sweetener that is derived from an amino acid. In further embodiments of the invention, the sweetener may not be a nutritive sweetener, a natural high-potency sweetener, a synthetic high-potency sweetener that is a glycoside or a synthetic high-potency sweetener that is derived from amino acids.

In yet further embodiments of the invention, the sweetener and the flavour enhancer cannot be identical.

In an embodiment of the present invention, the at least one sweetener of the sweetener composition may be selected from the group consisting of a nutritive sweetener (e.g. a 3- to 12-carbon sugar alcohol, a monosaccharide and a sweet disaccharide, such as allose, deoxyribose, erythrulose, galactose, gulose, idose, lyxose, mannose, ribose, tagatose, talose, xylose, erythrose, fuculose, gentiobiose, gentiobiulose, isomaltose, isomaltulose, kojibiose, lactulose, altrose, laminaribiose, arabinose, leucrose, fucose, rhamnose, sorbose, maltulose, mannobiose, mannosucrose, melezitose, melibiose, melibiulose, nigerose, raffinose, rutinose, rutinulose, sophorose, stachyose, threose, trehalose, trehalulose, turanose, xylobiose, glucose-fructose syrup, invert sugar, arabitol, glycerol, hydrogenated starch hydrolysate, isomalt, lactitol, maltitol, mannitol, sorbitol and xylitol; allulose (also known as D-psicose), high fructose corn syrup, glucose, erythritol, fructose, sucrose), aspartame, or particularly, acesulfame, cyclamate, saccharin and sucralose, and salts and/or solvates thereof. Particular salts of acesulfame that may be mentioned in embodiments of the present invention include potassium and sodium salts thereof.

In a preferred embodiment, the at least one sweetener of the sweetener composition may be selected from the group consisting of allulose, fructose, high fructose corn syrup, glucose and erythritol, aspartame, particularly, sucrose, or more particularly, acesulfame, cyclamate, saccharin and sucralose; and salts and/or solvates thereof. In a further preferred embodiment, the at least one sweetener of the sweetener composition may be sucralose.

In a further embodiment of the present invention, the at least one flavour enhancer may be selected from the group consisting of abrusoside A, alitame, aspartame, baiyunoside, brazzein, curculin, cyclocarioside I, glycyphyllin, glycyrrhizic acid, hernandulcin, N—[N-[3-(3-hydroxy-4-methoxyphenyl)propyl]-L-[alpha]-aspartyl]-L-phenylalanine 1-methyl ester, N—[N-[3-(3-hydroxy-4-methoxyphenyl)-3-methylbutyl]-L-[alpha]-aspartyl]-L-phenylalanine 1-methyl ester, a Luo Han Guo extract, mabinlin, N—[N-[3-(3-methoxy-4-hydroxyphenyl)propyl]-L-[alpha]-aspartyl]-L-phenylalanine 1-methyl ester, monatin, monellin, mukurozioside, neohesperidin dihydrochalcone, neotame, osladin, periandrins, phlomisosides, phloridzin, phyllodulcin, polypodoside A, pterocaryoside A, pterocaryoside B, an ent-kaurane sweetener (e.g. a stevia extract, glucosylated steviol glycosides, steviol glycosides, rubusoside, or a rebaudioside, such as rebaudioside A to F, M, N and X), thaumatin and trilobatin, and salts and/or solvates thereof.

In an alternative embodiment, the at least one flavour enhancer may be selected from the group consisting of abrusoside A, aspartame, baiyunoside, cyclocarioside I, glycyphyllin, glycyrrhizic acid, a glucosylated steviol glycoside, a Luo Han Guo extract, monatin, mukurozioside, neohesperidin dihydrochalcone, neotame, osladin, periandrins, phlomisosides, phloridzin, polypodoside A, pterocaryoside A, pterocaryoside B, a stevia extract, a steviol glycoside, a glucosylated steviol glycoside, rubusoside and trilobatin, and salts and/or solvates thereof. For example, the at least one flavour enhancer may be selected from the group consisting of a Luo Han Guo extract, neohesperidin dihydrochalcone, neotame and a stevia extract, and salts and/or solvates thereof.

In a preferred embodiment, the at least one flavour enhancer may be selected from the group consisting of neohesperidin dihydrochalcone and neotame.

In embodiments where the at least one sweetener comprises at least one nutritive sweetener and at least one high potency sweetener selected from the group consisting of aspartame, acesulfame, cyclamate, saccharin and sucralose, and salts and/or solvates thereof, the ratio of the at least one high potency sweetener to the nutritive sweetener in the sweetener composition is from about 0.01:1 to about 6.25:1 on a weight to weight basis. For example, the ratio of the at least one high potency sweetener to the nutritive sweetener is greater than about 0.015:1 and less than or equal to about 2:1 or is from about 0.02:1 to about 0.5:1 on a weight to weight basis.

In alternative embodiments, the ratio of the at least one high potency sweetener to the nutritive sweetener is from about 0.025:1 to about 0.25:1 on a weight to weight basis.

In alternative embodiments of the invention, when the at least one sweetener comprises at least one nutritive sweetener and at least one high potency sweetener selected from the group consisting of aspartame, acesulfame, cyclamate, saccharin and sucralose, and salts and/or solvates thereof, the ratio of the at least one high potency sweetener to the at least one nutritive sweetener is from about 0.01:1 to about 0.1:1 on a weight to weight basis. For example, the ratio of the at least one high potency sweetener to the at least one nutritive sweetener may be greater than about 0.015:1 and less than or equal to about 0.05:1, from about 0.02:1 to about 0.04:1 or, particularly, from about 0.025:1 to about 0.035:1 on a weight to weight basis.

In preferred embodiments, the ratio of the at least one high potency sweetener to the nutritive sweetener is about 0.03:1 on a weight to weight basis.

In embodiments, the at least one anti-foaming agent of the sweetener composition comprises one or more selected from the group consisting of a fatty acid, a fatty acid ester, a silicone oil, silicon dioxide, an alkyl-substituted silicon dioxide, lecithin, a vegetable oil, propylene glycol mono and diesters of fatty acids, propylene glycol alginate, calcium alginate, mineral oil, odourless light petroleum hydrocarbons, petrolatum, petroleum waxes, synthetic isoparaffinic petroleum hydrocarbons, synthetic petroleum wax, paraffin wax, microcrystalline wax, tallow, oxidized tallow, sulfated tallow, oleomargarine, lard, butter, oxystearin, a fatty acid metal salt, ethylene oxide polymer, copolymer condensates of ethylene oxide and propylene oxide, polyethylene glycol, polypropylene glycol, polyethylene glycol (400) dioleate, sorbitan monostearate, polysorbate 60 (polyoxyethylene (20) sorbitan monostearate), polysorbate 65 (polyoxyethylene (20) sorbitan tristearate), polysorbate 80 (polyoxyethylene (20) sorbitan monooleate), n-butoxypolyoxyethylene polyoxypropylene glycol, polyoxyethylene (600) dioleate, polyoxyethylene (600) monoricinoleate and polyoxyethylene (40) monostearate. For example, anti-foaming agents that may be mentioned herein include a fatty acid, a fatty acid ester, a silicone oil, silicon dioxide, an alkyl-substituted silicon dioxide, lecithin, a vegetable oil, propylene glycol mono and diesters of fatty acids, propylene glycol alginate and calcium alginate.

In alternative embodiments, the at least one anti-foaming agent comprises one or more selected from the group consisting of decanoic acid, oleic acid, capric acid, caprylic acid, lauric acid, myristic acid, palmitic acid, stearic acid, a fatty acid ester, a silicone oil, silicon dioxide, an alkyl-substituted silicon dioxide, corn oil, coconut oil and cottonseed oil.

The term "alkyl-substituted silicon dioxide" as used herein refers to a solid silicon dioxide polymer where one or two oxygen atoms attached to one or more silicon atoms have been replaced by an alkyl group (e.g. a methyl or ethyl group).

The term "silicone oil" refers to any liquid polymerised siloxane with organic side chains. They are formed with a backbone of alternating silicon-oxygen atoms ( . . . Si—O—Si—O—Si . . . ) where the organic side chains are attached to the silicon atoms. Examples of silicone oils include polydimethylsiloxane and hexamethyldisiloxane.

In preferred embodiments, the at least one anti-foaming agent comprises one or more selected from the group consisting of polydimethylsiloxane, a fatty acid ester, silicon dioxide, corn oil, coconut oil and cottonseed oil.

The term "a fatty acid ester" as used herein refers to an alkyl ester of decanoic acid, oleic acid, capric acid, caprylic acid, lauric acid, myristic acid, palmitic acid, stearic acid (e.g. methyl, ethyl, propyl or butyl esters of said fatty acids). Preferably, the fatty acid ester comprises butyl stearate.

In preferred embodiments, the at least one anti-foaming agent comprises polydimethylsiloxane or a combination of polydimethylsiloxane and silicon dioxide.

In embodiments, the at least one anti-foaming agent has a hydrophilic-lipophilic balance value of less than or equal to 10.

The term "hydrophilic-lipophilic balance" as used herein relates to the measurement of the degree to which a compound is hydrophilic or lipophilic, determined by calculating values for the different regions of the molecule, as described by Griffin (Griffin, W. C. (1949), *Journal of the Society of Cosmetic Chemists* 1 (5): 311-26 and Griffin, William C. (1954), *Journal of the Society of Cosmetic Chemists* 5 (4): 249-56). This method requires the use of Formula A below:

$$\text{Hydrophilic-lipophilic balance} = 20 \times M_h / M \quad (A),$$

where $M_h$ is the molecular mass of the hydrophilic portion of the molecule, and M is the molecular mass of the whole molecule, giving a result on a scale of 0 to 20. A hydrophilic-lipophilic balance value of 0 corresponds to a completely lipophilic/hydrophobic molecule, and a value of 20 corresponds to a completely hydrophilic/lipophobic molecule. In general, a value of 10 or below corresponds to a lipid soluble (water insoluble) molecule.

In further embodiments, the ratio of the at least one flavour enhancer to the at least one anti-foaming agent is from about 0.01:1 to about 100:1 on a weight to weight basis. For example, the ratio of the at least one flavour enhancer to the at least one anti-foaming agent may be from about 0.1:1 to about 50:1 on a weight to weight basis. In particular embodiments, the ratio of the at least one flavour enhancer to the at least one anti-foaming agent is from about 0.04:1 to about 40:1 (e.g. about 0.4:1 to about 40:1) on a weight to weight basis. For example, the ratio of the at least one flavour enhancer to the at least one anti-foaming agent may be from about 0.5:1 to about 2.5:1 or from about 1:1 to 2:1 on a weight to weight basis.

In alternative embodiments, the ratio of the at least one flavour enhancer to the at least one anti-foaming agent may be from about 2:1 or about 1.9:1 on a weight to weight basis.

In yet further embodiments, the ratio of the at least one flavour enhancer to the at least one anti-foaming agent is from about 0.004:1 to about 100:1 on a weight to weight basis. For example, the ratio of the at least one flavour enhancer to the at least one anti-foaming agent is from about 0.008:1 to about 100:1 on a weight to weight basis. In particular embodiments the ratio of the at least one flavour enhancer to the at least one anti-foaming agent is from about 0.008:1 to about 50:1 on a weight to weight basis. For example, the ratio of the at least one flavour enhancer to the at least one anti-foaming agent is from about 0.008:1 to about 40:1 on a weight to weight basis.

Alternatively, the ratio of the at least one flavour enhancer to the at least one anti-foaming agent is from about 0.01:1 to about 40:1, or from about 0.05:1 to about 40:1 on a weight to weight basis.

In further embodiments, when the at least one sweetener comprises at least one nutritive sweetener and at least one high potency sweetener selected from the group consisting of aspartame, acesulfame, cyclamate, saccharin and sucralose, and salts and/or solvates thereof, the ratio of the at least one high potency sweetener to the nutritive sweetener is from about 0.01:1 to about 6.25:1 on a weight to weight basis (preferably greater than about 0.015:1 and less than or equal to about 2:1, more preferably from about 0.02:1 to about 0.5:1 or even more preferably from about 0.025:1 to about 0.25:1 (e.g. about 0.03:1) on a weight to weight basis) and the ratio of the at least one flavour enhancer to the at least one anti-foaming agent is from about 0.01:1 to about 100:1 on a weight to weight basis (preferably from about 0.1:1 to about 50:1, more preferably from about 0.4:1 to about 40:1, or more preferably from about 0.5:1 to about 2.5:1 (e.g. about 1.9:1 or about 2.1:1) on a weight to weight basis).

In further embodiments, when the at least one sweetener comprises at least one nutritive sweetener and at least one high potency sweetener selected from the group consisting of aspartame, acesulfame, cyclamate, saccharin and sucralose, and salts and/or solvates thereof, the ratio of the at least one high potency sweetener to the nutritive sweetener is from about 0.01:1 to about 0.1:1 on a weight to weight basis (preferably greater than about 0.015:1 and less than or equal to about 0.05:1, more preferably from about 0.02:1 to about 0.04:1 or even more preferably from about 0.025:1 to about 0.035:1 (e.g. about 0.03:1) on a weight to weight basis) and the ratio of the at least one flavour enhancer to the at least one anti-foaming agent is from about 0.01:1 to about 100:1 on a weight to weight basis (preferably from about 0.1:1 to about 50:1, more preferably from about 0.4:1 to about 40:1, more preferably from about 0.5:1 to about 2.5:1 (e.g. about 1.9:1 or about 2.1:1) on a weight to weight basis).

In further embodiments, when the at least one sweetener comprises at least one nutritive sweetener and at least one high potency sweetener selected from the group consisting of aspartame, acesulfame, cyclamate, saccharin and sucralose, and salts and/or solvates thereof; the at least one flavour enhancer is selected from the group consisting of the abrusoside A, aspartame, baiyunoside, cyclocarioside I, glycyphyllin, glycyrrhizic acid, a glucosylated steviol glycoside, a Luo Han Guo extract, monatin, mukurozioside, neohesperidin dihydrochalcone, neotame, osladin, periandrins, phlomisosides, phloridzin, polypodoside A, pterocaryoside A, pterocaryoside B, a *stevia* extract, a steviol glycoside, rubusoside and trilobatin, and salts and/or solvates thereof; and the at least one anti-foaming agent is selected from the group consisting of a fatty acid (e.g. decanoic acid, oleic acid, capric acid, caprylic acid, lauric acid, myristic acid, palmitic acid and stearic acid), a fatty acid ester, a silicone oil, silicon dioxide, an alkyl-substituted silicon dioxide, lecithin, a vegetable oil, propylene glycol mono and diesters of fatty acids, propylene glycol alginate and calcium alginate, the ratio of the at least one high potency sweetener to the nutritive sweetener is from about 0.01:1 to about 6.25:1 on a weight to weight basis (preferably greater than about 0.015:1 and less than or equal to about 2:1, more preferably from about 0.02:1 to about 0.5:1 or even more preferably from about 0.025:1 to about 0.25:1 (e.g. about 0.03:1) on a weight to weight basis) and the ratio of the at least one flavour enhancer to the at least one anti-foaming agent is from about 0.01:1 to about 100:1 on a weight to weight basis (preferably from about 0.1:1 to about 50:1, more preferably from about 0.4:1 to about 40:1, or more preferably from about 0.5:1 to about 2.5:1 (e.g. about 1.9:1 or about 2.1:1) on a weight to weight basis).

In further embodiments, when the at least one sweetener comprises at least one nutritive sweetener and at least one high potency sweetener selected from the group consisting of aspartame, acesulfame, cyclamate, saccharin and sucralose, and salts and/or solvates thereof; the at least one flavour enhancer is selected from the group consisting of the abrusoside A, aspartame, baiyunoside, cyclocarioside I, glycyphyllin, glycyrrhizic acid, a glucosylated steviol glycoside, a Luo Han Guo extract, monatin, mukurozioside, neohesperidin dihydrochalcone, neotame, osladin, periandrins, phlomisosides, phloridzin, polypodoside A, pterocaryoside A, pterocaryoside B, a *stevia* extract, a steviol glycoside, rubusoside and trilobatin, and salts and/or solvates thereof; and the at least one anti-foaming agent is selected from the group consisting of a fatty acid (e.g. decanoic acid, oleic acid, capric acid, caprylic acid, lauric acid, myristic acid, palmitic acid and stearic acid), a fatty acid ester, a silicone oil, silicon dioxide, an alkyl-substituted silicon dioxide, lecithin, a vegetable oil, propylene glycol mono and diesters of fatty acids, propylene glycol alginate and calcium alginate, the ratio of the at least one high potency sweetener to the nutritive sweetener is from about 0.01:1 to about 0.1:1 on a weight to weight basis (preferably greater than about 0.015:1 and less than or equal to about 0.05:1, more preferably from about 0.02:1 to about 0.04:1 or even more preferably from about 0.025:1 to about 0.035:1 (e.g. about 0.03:1) on a weight to weight basis) and the ratio of the at least one flavour enhancer to the at least one anti-foaming agent is from about 0.01:1 to about 100:1 on a weight to weight basis (preferably from about 0.1:1 to about 50:1, more preferably from about 0.4:1 to about 40:1, or more preferably from about 0.5:1 to about 2.5:1 (e.g. about 1.9:1 or about 2.1:1) on a weight to weight basis).

In further embodiments, when the at least one sweetener comprises at least one nutritive sweetener and at least one high potency sweetener selected from the group consisting of aspartame, acesulfame, cyclamate, saccharin and sucralose, and salts and/or solvates thereof; the at least one flavour enhancer is selected from the group consisting of a Luo Han Guo extract, neohesperidin dihydrochalcone, neotame, and a *stevia* extract and salts and/or solvates thereof; and the at least one anti-foaming agent is selected from the group consisting of polydimethylsiloxane, a fatty acid ester, silicon dioxide, corn oil, coconut oil and cottonseed oil, the ratio of the at least one high potency sweetener to the nutritive sweetener is greater than about 0.015:1 and less than or equal to about 2:1 (preferably from about 0.02:1 to about 0.5:1 or even more preferably from about 0.025:1 to about 0.25:1 (e.g. about 0.03:1) on a weight to weight basis) and the ratio of the at least one flavour enhancer to the at least one anti-foaming agent is from about 0.01:1 to about 100:1 on a weight to weight basis (preferably from about 0.1:1 to about 50:1, more preferably from about 0.4:1 to about 40:1, or more preferably from about 0.5:1 to about 2.5:1 (e.g. about 1.9:1 or about 2.1:1) on a weight to weight basis).

In further embodiments, when the at least one sweetener comprises at least one nutritive sweetener and at least one high potency sweetener selected from the group consisting of aspartame, acesulfame, cyclamate, saccharin and sucralose, and salts and/or solvates thereof; the at least one flavour enhancer is selected from the group consisting of a Luo Han Guo extract, neohesperidin dihydrochalcone, neotame, and a *stevia* extract and salts and/or solvates thereof; and the at least one anti-foaming agent is selected from the group consisting of polydimethylsiloxane, a fatty acid ester, silicon dioxide, corn oil, coconut oil and cottonseed oil, the ratio of the at least one high potency sweetener to the nutritive sweetener is greater than about 0.015:1 and less than or equal to about 0.05:1 on a weight to weight basis (preferably from about 0.02:1 to about 0.04:1 or even more preferably from about 0.025:1 to about 0.035:1 (e.g. about 0.03:1) on a weight to weight basis) and the ratio of the at least one flavour enhancer to the at least one anti-foaming agent is from about 0.01:1 to about 100:1 on a weight to weight basis (preferably from about 0.1:1 to about 50:1, more preferably from about 0.4:1 to about 40:1, or more preferably from about 0.5:1 to about 2.5:1 (e.g. about 1.9:1 or about 2.1:1) on a weight to weight basis).

In further embodiments, when the at least one sweetener comprises at least one nutritive sweetener and at least one high potency sweetener selected from the group consisting of aspartame, acesulfame, cyclamate, saccharin and sucralose, and salts and/or solvates thereof; the at least one flavour enhancer is selected from the group consisting of a neohesperidin dihydrochalcone and neotame; and the at least one anti-foaming agent is selected from the group consisting of polydimethylsiloxane and silicon dioxide, the ratio of the at least one high potency sweetener to the nutritive sweetener is greater than about 0.015:1 and less than or equal to about 2:1 (preferably from about 0.02:1 to about 0.5:1, more preferably from about 0.025:1 to about 0.25:1, or even more preferably from about 0.025:1 to about 0.08:1 (e.g. about 0.03:1) on a weight to weight basis) and the ratio of the at least one flavour enhancer to the at least one anti-foaming agent is from about 0.01:1 to about 100:1 on a weight to weight basis (preferably from about 0.1:1 to about 50:1, more preferably from about 0.4:1 to about 40:1, or more preferably from about 0.5:1 to about 2.5:1 (e.g. about 1.9:1 or about 2.1:1) on a weight to weight basis).

In further embodiments, when the at least one sweetener comprises at least one nutritive sweetener and at least one high potency sweetener selected from the group consisting of aspartame, acesulfame, cyclamate, saccharin and sucralose, and salts and/or solvates thereof; the at least one flavour enhancer is selected from the group consisting of a neohesperidin dihydrochalcone and neotame; and the at least one anti-foaming agent is selected from the group consisting of polydimethylsiloxane and silicon dioxide, the ratio of the at least one high potency sweetener to the nutritive sweetener is greater than about 0.015:1 and less than or equal to about 0.05:1 (preferably from about 0.02:1 to about 0.04:1, more preferably from about 0.025:1 to about 0.035:1 (e.g. about 0.03:1) on a weight to weight basis) and the ratio of the at least one flavour enhancer to the at least one anti-foaming agent is from about 0.01:1 to about 100:1 on a weight to weight basis (preferably from about 0.1:1 to about 50:1, more preferably from about 0.4:1 to about 40:1, or more preferably from about 0.5:1 to about 2.5:1 (e.g. about 1.9:1 or about 2.1:1) on a weight to weight basis).

In further embodiments, when the at least one sweetener comprises at least one nutritive sweetener and at least one high potency sweetener selected from the group consisting of aspartame, acesulfame, cyclamate, saccharin and sucralose, and salts and/or solvates thereof; the at least one flavour enhancer is selected from the group consisting of a neohesperidin dihydrochalcone and neotame; and the at least one anti-foaming agent is selected from the group consisting of polydimethylsiloxane and silicon dioxide, the ratio of the at least one high potency sweetener to the nutritive sweetener is greater than about 0.015:1 and less than or equal to about 0.05:1 (preferably from about 0.02:1 to about 0.04:1, more preferably from about 0.025:1 to about 0.035:1 (e.g. about 0.03:1) on a weight to weight basis) and the ratio of the at least one flavour enhancer to the at least one anti-foaming agent is from about 0.004:1 to about 100:1 on a weight to weight basis (preferably from about 0.008:1 to about 100:1, more preferably from about 0.008:1 to about 50:1, or more preferably from about 0.008:1 to about 40:1 on a weight to weight basis).

In yet further embodiments, when the at least one sweetener comprises at least one nutritive sweetener and sucralose, and salts and/or solvates thereof; the at least one flavour enhancer is selected from the group consisting of a neohesperidin dihydrochalcone and neotame; and the at least one anti-foaming agent is selected from the group consisting of polydimethylsiloxane and silicon dioxide, the ratio of the at least one high potency sweetener to the nutritive sweetener is greater than about 0.015:1 and less than or equal to about 2:1 (preferably from about 0.02:1 to about 0.5:1, more preferably from about 0.025:1 to about 0.25:1, or even more preferably from about 0.025:1 to about 0.08:1 (e.g. about 0.03:1) on a weight to weight basis) and the ratio of the at least one flavour enhancer to the at least one anti-foaming agent is from about 0.01:1 to about 100:1 on a weight to weight basis (preferably from about 0.1:1 to about 50:1, more preferably from about 0.4:1 to about 40:1, or more preferably from about 0.5:1 to about 2.5:1 (e.g. about 1.9:1 or about 2.1:1) on a weight to weight basis).

In yet further embodiments, when the at least one sweetener comprises at least one nutritive sweetener and sucralose, and salts and/or solvates thereof; the at least one flavour enhancer is selected from the group consisting of a neohesperidin dihydrochalcone and neotame; and the at least one anti-foaming agent is selected from the group consisting of polydimethylsiloxane and silicon dioxide, the ratio of the at least one high potency sweetener to the nutritive sweetener is greater than about 0.015:1 and less than or equal to about 2:1 (preferably from about 0.02:1 to about 0.5:1, more preferably from about 0.025:1 to about 0.25:1, or even more preferably from about 0.025:1 to about 0.08:1 (e.g. about 0.03:1) on a weight to weight basis) and the ratio of the at least one flavour enhancer to the at least one anti-foaming agent is from about 0.004:1 to about 100:1 on a weight to weight basis (preferably from about 0.008:1 to about 100:1, more preferably from about 0.008:1 to about 50:1, or more preferably from about 0.008:1 to about 40:1 on a weight to weight basis).

In yet further embodiments, when the at least one sweetener comprises at least one nutritive sweetener and sucralose, and salts and/or solvates thereof; the at least one flavour enhancer is selected from the group consisting of a neohesperidin dihydrochalcone and neotame; and the at least one anti-foaming agent is selected from the group consisting of polydimethylsiloxane and silicon dioxide, the ratio of the at least one high potency sweetener to the nutritive sweetener is greater than about 0.015:1 and less than or equal to about 0.05:1 (preferably from about 0.02:1 to about 0.04:1, more preferably from about 0.025:1 to about 0.035:1 (e.g. about 0.03:1) on a weight to weight basis) and the ratio of the at least one flavour enhancer to the at least one anti-foaming agent is from about 0.01:1 to about 100:1 on a weight to weight basis (preferably from about 0.1:1 to about 50:1, more preferably from about 0.4:1 to about 40:1, or more preferably from about 0.5:1 to about 2.5:1 (e.g. about 1.9:1 or about 2.1:1) on a weight to weight basis).

In yet further embodiments, when the at least one sweetener comprises at least one nutritive sweetener and sucralose, and salts and/or solvates thereof; the at least one flavour enhancer is selected from the group consisting of a neohesperidin dihydrochalcone and neotame; and the at least one anti-foaming agent is selected from the group consisting of polydimethylsiloxane and silicon dioxide, the ratio of the at least one high potency sweetener to the nutritive sweetener is greater than about 0.015:1 and less than or equal to about 0.05:1 (preferably from about 0.02:1 to about 0.04:1, more preferably from about 0.025:1 to about 0.035:1 (e.g. about 0.03:1) on a weight to weight basis) and the ratio of the at least one flavour enhancer to the at least one anti-foaming agent is from about 0.004:1 to about 100:1 on a weight to weight basis (preferably from about 0.008:1 to about 100:1, more preferably from about 0.008:1 to about 50:1, or more preferably from about 0.008:1 to about 40:1 on a weight to weight basis).

In yet further embodiments, when the at least one sweetener comprises at least one nutritive sweetener (preferably selected from the group consisting of sucrose and fructose) and sucralose, and salts and/or solvates thereof; the at least one flavour enhancer is selected from the group consisting of a neohesperidin dihydrochalcone and neotame; and the at least one anti-foaming agent is selected from the group consisting of polydimethylsiloxane and silicon dioxide, the ratio of the at least one high potency sweetener to the nutritive sweetener is greater than about 0.015:1 and less than or equal to about 2:1 (preferably from about 0.02:1 to about 0.5:1, more preferably from about 0.025:1 to about 0.25:1, or even more preferably from about 0.025:1 to about 0.08:1 on a weight to weight basis) and the ratio of the at least one flavour enhancer to the at least one anti-foaming agent is from about 0.01:1 to about 100:1 on a weight to weight basis (preferably from about 0.1:1 to about 50:1, more preferably from about 0.4:1 to about 40:1, or more preferably from about 0.5:1 to about 2.5:1 (e.g. about 1.9:1 or about 2.1:1) on a weight to weight basis).

In yet further embodiments, when the at least one sweetener comprises at least one nutritive sweetener (preferably selected from the group consisting of sucrose and fructose) and sucralose, and salts and/or solvates thereof; the at least one flavour enhancer is selected from the group consisting of a neohesperidin dihydrochalcone and neotame; and the at least one anti-foaming agent is selected from the group consisting of polydimethylsiloxane and silicon dioxide, the ratio of the at least one high potency sweetener to the nutritive sweetener is greater than about 0.015:1 and less than or equal to about 2:1 (preferably from about 0.02:1 to about 0.5:1, more preferably from about 0.025:1 to about 0.25:1, or even more preferably from about 0.025:1 to about 0.08:1 on a weight to weight basis) and the ratio of the at least one flavour enhancer to the at least one anti-foaming agent is from about 0.004:1 to about 100:1 on a weight to weight basis (preferably from about 0.008:1 to about 100:1, more preferably from about 0.008:1 to about 50:1, or more preferably from about 0.008:1 to about 40:1 on a weight to weight basis).

In yet further embodiments, when the at least one sweetener comprises at least one nutritive sweetener (preferably selected from the group consisting of sucrose and fructose) and sucralose, and salts and/or solvates thereof; the at least one flavour enhancer is selected from the group consisting of a neohesperidin dihydrochalcone and neotame; and the at least one anti-foaming agent is selected from the group consisting of polydimethylsiloxane and silicon dioxide, the ratio of the at least one high potency sweetener to the nutritive sweetener is greater than about 0.015:1 and less than or equal to about 0.05:1 (preferably from about 0.02:1 to about 0.04:1, more preferably from about 0.025:1 to about 0.035:1 (e.g. about 0.03:1) on a weight to weight basis) and the ratio of the at least one flavour enhancer to the at least one anti-foaming agent is from about 0.01:1 to about 100:1 on a weight to weight basis (preferably from about 0.1:1 to about 50:1, more preferably from about 0.4:1 to about 40:1, or more preferably from about 0.5:1 to about 2.5:1 (e.g. about 1.9:1 or about 2.1:1) on a weight to weight basis).

In yet further embodiments, when the at least one sweetener comprises at least one nutritive sweetener (preferably selected from the group consisting of sucrose and fructose) and sucralose, and salts and/or solvates thereof; the at least one flavour enhancer is selected from the group consisting of a neohesperidin dihydrochalcone and neotame; and the at least one anti-foaming agent is selected from the group consisting of polydimethylsiloxane and silicon dioxide, the ratio of the at least one high potency sweetener to the nutritive sweetener is greater than about 0.015:1 and less than or equal to about 0.05:1 (preferably from about 0.02:1 to about 0.04:1, more preferably from about 0.025:1 to about 0.035:1 (e.g. about 0.03:1) on a weight to weight basis) and the ratio of the at least one flavour enhancer to the at least one anti-foaming agent is from about 0.004:1 to about 100:1 on a weight to weight basis (preferably from about 0.008:1 to about 100:1, more preferably from about 0.008:1 to about 50:1, or more preferably from about 0.008:1 to about 40:1 on a weight to weight basis).

Typically, the sweetener composition is formulated as a syrup, in powder form, in tablet form, as granules, or as a solution.

In a second aspect of the present invention, there is provided a sweetener composition comprising:
a sweetener comprising sucralose;
an anti-foaming agent comprising polydimethylsiloxane and/or silicon dioxide; and
a flavour enhancer comprising neohesperidin dihydrochalcone and neotame, wherein the flavour enhancer is used in an amount below its sweetness threshold.

In embodiments of the second aspect, the composition may further comprise a nutritive sweetener selected from one or more of the group consisting of fructose and sucrose. In certain embodiments of the second aspect of the present invention, the ratio of the at least one flavour enhancer to the at least one anti-foaming agent is about 0.4:1 or about 0.38:1 on a weight to weight basis. In other embodiments, the ratio of the at least one flavour enhancer to the at least one anti-foaming agent is about 2:1 or about 1.9:1 on a weight to weight basis.

A further aspect relates to a product for human and/or animal consumption that comprises the sweetener composition hereinbefore defined. Typically, the product may be a food product, a beverage product, a pharmaceutical product, a nutritional product, a sports product, or a cosmetic product.

It will be appreciated that the amount of the sweetener composition of the invention present in a food product, a beverage product, a pharmaceutical product, a nutritional product, a sports product, or a cosmetic product, will depend upon the type and amount of sweetener present in the sweetener composition and the desired sweetness of the food or beverage product.

When the product is a food product, the product may be selected from the group consisting of a confectionary product, a dessert product, a cereal product, baked goods, frozen dairy products, meats, dairy products, condiments, snack bars, soups, dressings, mixes, prepared foods, baby foods, diet preparations, syrups, food coatings, dried fruit, sauces, gravies, and jams/jellies. When the sweetener composition hereinbefore defined is applied to any of the food product listed above, it may be applied as a coating or frosting formed on the surface of the product. This coating may be useful to improve the flavour of the food product as well as its shelf life.

When the product is a beverage product, the product may be selected from the group consisting of a concentrated beverage mix (e.g. MiO®, Dasani Drops® and powdered soft drinks), a carbonated beverage, a non-carbonated beverage, fruit-flavoured beverage, fruit-juice, tea, milk, coffee, and the like. In certain embodiments of the invention, the beverage product may not be a carbonated beverage.

In certain embodiments, the beverage product comprises a nutritive sweetener at a concentration of less than 5000 ppm. Alternatively or additionally, the concentration of the nutritive sweetener in the beverage product is greater than or equal to 80 ppm.

In further embodiments, the beverage product has an acidic pH. Typically, the pH is from about 2.0 to about 6.5.

In further embodiments of the product for human and/or animal consumption, the sweetness onset time and/or sweet taste linger may have been shortened relative to a product comprising the high potency sweetener alone.

In a further aspect of the present invention, there is provided a use of at least one anti-foaming agent and at least one flavour enhancer to shorten the sweetness onset time and/or the sweetness linger of at least one sweetener, wherein the flavour enhancer is at least one high potency sweetener that contains hydrophilic and hydrophobic structural moieties; and the flavour enhancer is used in an amount below its sweetness threshold. Alternatively, there is provided a use of at least one anti-foaming agent and at least one flavour enhancer to shorten the sweetness onset time and/or the sweetness linger of at least one sweetener, wherein the flavour enhancer is selected from a natural high-potency sweetener, a synthetic high-potency sweetener that is a glycoside or a synthetic high-potency sweetener that is derived from amino acids; and the flavour enhancer is used in an amount below its sweetness threshold. In this aspect, each of the terms listed uses the meanings hereinbefore defined.

A fifth aspect of the invention provides a method of making a sweetener composition according to the first or second aspect of the invention, said method comprising mixing at least one sweetener with at least one anti-foaming agent and at least one flavour enhancer.

The mixing of the various solid components together may be conducted using any known technique. Particular techniques for the mixing that may be mentioned include the use of a Turbula® mixer, a drum tumbler mixer or static mixers. Other mixing techniques may also be used.

In embodiments of the fifth aspect, the mixing of the at least one sweetener with the at least one anti-foaming agent and the at least one flavour enhancer may be accomplished by sequential or concomitant mixing.

The following examples are exemplary only and are not intended to be limiting in any way.

EXAMPLES

Example 1

Improvement of the Temporal Profile of Sucralose by the Use of Small Amounts of a High Potency Sweetener and an Anti-Foaming Agent This experiment determines if temporal modifiers can change the sweetness profile of sucralose as a single sweetening agent or when used in blends with other high potency sweeteners that are used at below their sweetness threshold. In this experiment, the high potency sweeteners neohesperidin dihydrochalcone and neotame were used at below their sweetness threshold level as flavours. In other words, this experiment looked at the ability of flavour levels (i.e. at a level below their sweetness threshold) of these high potency sweeteners to enhance the flavour and/or temporal profile of sucralose.

The temporal profile was completed with a trained descriptive panel. Panellists had several orientation rounds of the test samples as well as other samples to familiarize themselves with the protocol and the samples. The tests were conducted as complete block designs in 3 replicates with the trained panel and were done over two testing days (one for each formula set). The presentation order was rotated. The solutions were served in 2 ounce soufflé cups labelled with 3-digit codes. Panellists were instructed to sample the product by placing the sample in their mouths and swallowing or spitting out the sample immediately while starting their intensity rating for sweetness at the same time using Eye-Question. Intensity ratings for sweetness were collected for 2 minutes. Panellists had a two minute wait time between samples and at least a 10 minute break in-between repetitions. Panellists cleaned their palates with bottled water and unsalted crackers.

The maximum intensity of each panellist for each sample was determined, and the overall temporal profile data for that sample was normalized as a % of maximum. Once normalized data is calculated, averaged response was calculated as a normalized % of maximum for each time point were normalized as a % of averaged normalized maximum and plotted for each sample. The details for each sample are set out below in Table 1.

"Sucralose plus" or "sucralose+" is the combination of sucralose with neohesperidin dihydrochalcone and neotame. TEMP in this example is the combination of the anti-foaming agent MD-20-S FG (which is a material that comprises 20 wt % of polydimethylsiloxane and silicon dioxide (as anti-foaming agents) and 80 wt % maltodextrin) with the sugar fructose.

TABLE 1

| | | Comparative Examples | | | |
|---|---|---|---|---|---|
| Ingredient | Supplier | Sucralose Grams (%) | Sucralose and TEMP Grams (%) | Sucralose + Grams (%) | Sucralose + with TEMP Grams (%) |
| Water | | 1499.465 (99.96433) | 1491.890 (99.45933) | 1499.7465 (99.98310) | 1492.1715 (99.47810) |
| Sucralose | T&L | 0.53500 (0.03567) | 0.53500 (0.03567) | 0.22500 (0.01500) | 0.22500 (0.01500) |
| Fructose, Crystalline | T&L | 0 (0) | 7.50000 (0.50) | 0 (0) | 7.50000 (0.50) |
| MD-20-S FG | Magrabar | 0 (0) | 0.07500 (0.005) | 0 (0) | 0.07500 (0.005) |
| Neotame | | 0 (0) | 0 (0) | 0.00600 (0.00040) | 0.00600 (0.00040) |
| NHDC | | 0 (0) | 0 (0) | 0.02250 (0.00150) | 0.02250 (0.00150) |
| TOTAL | | 1500 (100) | 1500 (100) | 1500 (100) | 1500 (100) |

The results of Example 1 are graphically represented in FIGS. 1 to 6.

Sucralose plus had the longest temporal linger which, without wishing to be bound by a theory, may be due to the sweet linger impact of the flavour modifiers (see FIG. 1). The addition of TEMP to sucralose plus improved both the upfront sweetness and reduced the linger of sucralose plus in this study (see FIGS. 5 and 6).

Addition of TEMP to just sucralose only slightly improved the temporal onset when compared to sucralose alone. TEMP with sucralose also only slightly reduced overall temporal linger compared to sucralose alone (see FIG. 3). However, the addition of TEMP and the flavouring levels of the high potency sweeteners mentioned above had a profound effect on the temporal profile of sucralose plus (see FIG. 2).

The invention claimed is:

1. A sweetener composition comprising:
at least one sweetener;
at least one anti-foaming agent; and
at least one flavour enhancer, wherein the flavour enhancer is:
at least one high potency sweetener, which is different from the aforementioned sweetener, that contains hydrophilic and hydrophobic structural moieties; and used in an amount below its sweetness threshold;
wherein the ratio of the at least one flavour enhancer to the at least one anti-foaming agent is from about 0.004:1 to about 100:1 on a weight to weight basis.

2. The sweetener composition of claim 1, wherein:
the flavour enhancer is selected from a natural high-potency sweetener, a synthetic high-potency sweetener that is a glycoside or a synthetic high-potency sweetener that is derived from an amino acid.

3. The composition of claim 1, wherein the at least one sweetener is selected from the group consisting of a nutritive sweetener, aspartame, acesulfame, cyclamate, saccharin and sucralose, and salts and/or solvates thereof.

4. The composition of claim 3, wherein the at least one sweetener is selected from the group consisting of a 3- to 12-carbon sugar alcohol, a monosaccharide, a sweet disaccharide, aspartame, acesulfame, cyclamate, saccharin and sucralose; and salts and/or solvates thereof.

5. The composition of claim 4, wherein the at least one sweetener is selected from the group consisting of allose, deoxyribose, erythrulose, galactose, gulose, idose, lyxose, mannose, ribose, tagatose, talose, xylose, erythrose, fuculose, gentiobiose, gentiobiulose, isomaltose, isomaltulose, kojibiose, lactulose, altrose, laminaribiose, arabinose, leucrose, fucose, rhamnose, sorbose, maltulose, mannobiose, mannosucrose, melezitose, melibiose, melibiulose, nigerose, raffinose, rutinose, rutinulose, sophorose, stachyose, threose, trehalose, trehalulose, turanose, xylobiose, glucose-fructose syrup, invert sugar, arabitol, glycerol, hydrogenated starch hydrolysate, isomalt, lactitol, maltitol, mannitol, sorbitol, xylitol, allulose, high fructose corn syrup, glucose, erythritol, fructose, sucrose, aspartame, acesulfame, cyclamate, saccharin and sucralose, and salts and/or solvates thereof.

6. The composition of claim 5, wherein the at least one sweetener is selected from the group consisting of sucrose, allulose, fructose, high fructose corn syrup, glucose and erythritol, aspartame, acesulfame, cyclamate, saccharin and sucralose; and salts and/or solvates thereof.

7. The composition of claim 6, wherein the at least one sweetener is selected from the group consisting of fructose, sucrose, acesulfame, cyclamate, saccharin and sucralose; and salts and/or solvates thereof.

8. The composition of claim 7, wherein the at least one sweetener is selected from the group consisting of acesulfame, cyclamate, saccharin and sucralose; and salts and/or solvates thereof.

9. The composition of claim 1, wherein the at least one sweetener comprises sucralose.

10. The composition of claim 1, wherein the at least one flavour enhancer is selected from the group consisting of abrusoside A, alitame, aspartame, baiyunoside, brazzein, curculin, cyclocarioside I, glycyphyllin, glycyrrhizic acid, hernandulcin, N—[N-[3-(3-hydroxy-4-methoxyphenyl)propyl]-L-[alpha]-aspartyl]-L-phenylalanine 1-methyl ester, N—[N-[3-(3-hydroxy-4-methoxyphenyl)-3-methylbutyl]-L-[alpha]-aspartyl]-L-phenylalanine 1-methyl ester, a Luo Han Guo extract, mabinlin, N— [N-[3-(3-methoxy-4-hydroxyphenyl)propyl]-L-[alpha]-aspartyl]-L-phenylalanine 1-methyl ester, monatin, monellin, mukurozioside, neohesperidin dihydrochalcone, neotame, osladin, periandrins, phlomisosides, phloridzin, phyllodulcin, polypodoside A, pterocaryoside A, pterocaryoside B, an ent-kaurane sweetener, thaumatin and trilobatin, and salts and/or solvates thereof.

11. The composition of claim 10, wherein the at least one flavour enhancer is selected from the group consisting of abrusoside A, aspartame, baiyunoside, cyclocarioside I, glycyphyllin, glycyrrhizic acid, a glucosylated steviol glycoside, a Luo Han Guo extract, monatin, mukurozioside, neohesperidin dihydrochalcone, neotame, osladin, periandrins, phlomisosides, phloridzin, polypodoside A, pterocaryoside A, pterocaryoside B, a *stevia* extract, a steviol glycoside, rubusoside and trilobatin, and salts and/or solvates thereof.

12. The composition of claim 11, wherein the at least one flavour enhancer is selected from the group consisting of a Luo Han Guo extract, neohesperidin dihydrochalcone, neotame and a stevia extract, and salts and/or solvates thereof.

13. The composition of claim 12, wherein the at least one flavour enhancer is selected from the group consisting of neohesperidin dihydrochalcone and neotame.

14. The composition of claim 3, wherein, when the at least one sweetener comprises at least one nutritive sweetener and at least one high potency sweetener selected from the group consisting of aspartame, acesulfame, cyclamate, saccharin and sucralose, and salts and/or solvates thereof, the ratio of the at least one high potency sweetener to the nutritive sweetener is from about 0.01:1 to about 6.25:1 on a weight to weight basis.

15. The composition of claim 14, wherein the ratio of the at least one high potency sweetener to the at least one nutritive sweetener is greater than about 0.015:1 and less than or equal to about 2:1 on a weight to weight basis.

16. The composition of claim 15, wherein the ratio of the at least one high potency sweetener to the at least one nutritive sweetener is from about 0.02:1 to about 0.5:1 on a weight to weight basis.

17. The composition of claim 16, wherein the ratio of the at least one high potency sweetener to the at least one nutritive sweetener is from about 0.025:1 to about 0.25:1 on a weight to weight basis.

18. The composition of claim 17, wherein the ratio of the at least one high potency sweetener to the at least one nutritive sweetener is about 0.03:1 on a weight to weight basis.

19. The composition of claim 1, wherein the at least one anti-foaming agent comprises one or more selected from the group consisting of a fatty acid, a fatty acid ester, a silicone oil, silicon dioxide, an alkyl-substituted silicon dioxide, lecithin, a vegetable oil, propylene glycol mono and diesters of fatty acids, propylene glycol alginate, calcium alginate, mineral oil, odourless light petroleum hydrocarbons, petrolatum, petroleum waxes, synthetic isoparaffinic petroleum hydrocarbons, synthetic petroleum wax, paraffin wax, microcrystalline wax, tallow, oxidized, or sulfated; oleomargarine, lard, butter, oxystearin, a fatty acid metal salt, ethylene oxide polymer, copolymer condensates of ethylene oxide and propylene oxide, polyethylene glycol, polypropylene glycol, polyethylene glycol (400) dioleate, sorbitan monostearate, polysorbate 60 (polyoxyethylene (20) sorbitan monostearate), polysorbate 65 (polyoxyethylene (20) sorbitan tristearate), polysorbate 80 (polyoxyethylene (20) sorbitan monooleate), n-butoxypolyoxyethylene polyoxypropylene glycol, polyoxyethylene (600) dioleate, polyoxyethylene (600) monoricinoleate and polyoxyethylene (40) monostearate.

20. The composition according to claim 19, wherein the at least one anti-foaming agent comprises one or more selected from the group consisting of a fatty acid, a fatty acid ester, a silicone oil, silicon dioxide, an alkyl-substituted silicon dioxide, lecithin, a vegetable oil, propylene glycol mono and diesters of fatty acids, propylene glycol alginate and calcium alginate.

21. The composition according to claim 20, wherein the at least one anti-foaming agent comprises one or more selected from the group consisting of decanoic acid, oleic acid, capric acid, caprylic acid, lauric acid, myristic acid, palmitic acid, stearic acid, a fatty acid ester, a silicone oil, silicon dioxide, an alkyl-substituted silicon dioxide, corn oil, coconut oil and cottonseed oil.

22. The composition according to claim 21, wherein the at least one anti-foaming agent comprises one or more selected from the group consisting of polydimethylsiloxane, a fatty acid ester, silicon dioxide, corn oil, coconut oil and cottonseed oil.

23. The composition according to claim 22, wherein the at least one anti-foaming agent comprises polydimethylsiloxane or a combination of polydimethylsiloxane and silicon dioxide.

24. The composition of claim 1, wherein each active ingredient of the at least one anti-foaming agent has a hydrophilic-lipophilic balance value of less than or equal to 10.

25. The composition of claim 1, wherein the ratio of the at least one flavour enhancer to the at least one anti-foaming agent is from about 0.4:1 to about 40:1 on a weight to weight basis.

26. The composition of claim 25, wherein the ratio of the at least one flavour enhancer to the at least one anti-foaming agent is from about 0.5:1 to 2.5:1 on a weight to weight basis.

27. The composition of claim 26, wherein the ratio of the at least one flavour enhancer to the at least one anti-foaming agent is about 1.9:1 on a weight to weight basis.

28. The composition of claim 26, wherein the ratio of the at least one flavour enhancer to the at least one anti-foaming agent is about 2:1 on a weight to weight basis.

29. The composition of claim 1, wherein the composition is formulated as a syrup, in powder form, in tablet form, as granules, or as a solution.

30. A product for human and/or animal consumption, comprising a composition according to claim 1.

31. The product of claim 30, wherein the product is a food product, a beverage product, a pharmaceutical product, a nutritional product, a sports product, or a cosmetic product.

32. The product of claim 31, wherein the product is a food product.

33. The product of claim 32, wherein the food product is selected from the group consisting of a confectionary product, a dessert product, a cereal product, baked goods, frozen dairy products, meats, dairy products, condiments, snack bars, soups, dressings, mixes, prepared foods, baby foods, diet preparations, syrups, food coatings, a frosting, dried fruit, sauces, gravies, and jams/jellies.

34. The product of claim 31, wherein the product is a beverage product.

35. The product of claim 34, wherein the beverage product is selected from the group consisting of a concentrated beverage mix, a carbonated beverage, a non-carbonated beverage, fruit-flavoured beverage, fruit-juice, tea, milk, coffee.

36. The product of claim 34, wherein the beverage product comprises a nutritive sweetener at a concentration of less than 5000 ppm.

37. The product of claim 34, wherein the concentration of the nutritive sweetener in the beverage product is greater than or equal to 80 ppm.

38. The product of claim 34, wherein the beverage product has an acidic pH.

39. The product of claim 38, wherein the pH is from about 2.0 to about 6.5.

40. A sweetener composition comprising:
a sweetener comprising sucralose;
an anti-foaming agent comprising polydimethylsiloxane and/or silicon dioxide; and
a flavour enhancer comprising neohesperidin dihydrochalcone and neotame, wherein the flavour enhancer is used in an amount below its sweetness threshold.

41. The sweetener composition of claim 40, wherein composition further comprises a nutritive sweetener selected from one or more of the group consisting of fructose and sucrose.

42. The sweetener composition of claim 40, wherein the ratio of the at least one flavour enhancer to the at least one anti-foaming agent is about 0.4:1 or about 0.38:1 on a weight to weight basis or the ratio of the at least one flavour enhancer to the at least one anti-foaming agent is about 2:1 or about 1.9:1 on a weight to weight basis.

43. A method of making a sweetener composition according to claim 1, said method comprising mixing at least one sweetener with at least one anti-foaming agent and at least one flavour enhancer.

44. The method of claim 43, wherein the mixing of the at least one sweetener with the at least one anti-foaming agent and the at least one flavour enhancer is accomplished by sequential or concomitant mixing.

* * * * *